United States Patent
Nguyen et al.

(10) Patent No.: US 9,955,893 B2
(45) Date of Patent: May 1, 2018

(54) METHODS, SYSTEMS, AND APPARATUS FOR IDENTIFICATION AND CHARACTERIZATION OF ROTORS ASSOCIATED WITH ATRIAL FIBRILLATION

(71) Applicant: AFTx, Inc., Westminster, CO (US)

(72) Inventors: Bao Nguyen, Westminster, CO (US); Jerome Edwards, Erie, CO (US); Paul Kessman, Lakewood, CO (US); Thomas Kurian, St. Louis, MO (US); Donald Conty, Jr., Denver, CO (US)

(73) Assignee: AFTX, Inc., Westminster, CO (US)

( * ) Notice: Subject to any disclaimer, the term of this patent is extended or adjusted under 35 U.S.C. 154(b) by 0 days. days.

(21) Appl. No.: 15/355,909

(22) Filed: Nov. 18, 2016

(65) Prior Publication Data
US 2017/0065195 A1 Mar. 9, 2017

Related U.S. Application Data

(63) Continuation of application No. 14/737,116, filed on Jun. 11, 2015, now Pat. No. 9,498,143, which is a (Continued)

(51) Int. Cl.
*A61B 5/02* (2006.01)
*A61B 5/00* (2006.01)
(Continued)

(52) U.S. Cl.
CPC .............. *A61B 5/046* (2013.01); *A61B 5/044* (2013.01); *A61B 5/04011* (2013.01);
(Continued)

(58) Field of Classification Search
USPC ......................................... 600/424, 508–509
See application file for complete search history.

(56) References Cited

U.S. PATENT DOCUMENTS

| 5,391,199 A | 2/1995 | Ben-Haim |
| 5,433,489 A | 7/1995 | Kimura et al. |

(Continued)

FOREIGN PATENT DOCUMENTS

| CN | 201759559 | 3/2011 |
| DE | 3908797 A1 | 9/1990 |

(Continued)

OTHER PUBLICATIONS

Office Action for U.S. Appl. No. 14/466,588, dated Nov. 17, 2014.
(Continued)

*Primary Examiner* — Nicole F Johnson
(74) *Attorney, Agent, or Firm* — Cooley LLP

(57) ABSTRACT

A system can include a near-field instrument to be placed inside a chamber of a heart, a far-field instrument to be placed in a stable position in relation to the heart, and a control unit. The control unit is configured to identify a unique pattern in electrogram information received from the far-field instrument when the near-field instrument is in one or more positions within the heart. When the unique pattern is detected, the control unit is configured to receive electrogram information from the near-field instrument. While recording electrogram information from the near-field instrument, the control unit is also configured to record voltage and complex fractionated atrial electrogram (CFAE) characteristics of the tissue inside a heart chamber. This information combined with rotor information can be used to identify substrate versus non-substrate rotor characteristics.

18 Claims, 17 Drawing Sheets

Related U.S. Application Data continuation of application No. 14/466,588, filed on Aug. 22, 2014, now Pat. No. 9,078,583.

(60) Provisional application No. 61/868,950, filed on Aug. 22, 2013, provisional application No. 61/988,651, filed on May 5, 2014.

(51) Int. Cl.
*A61B 5/046* (2006.01)
*A61B 5/042* (2006.01)
*A61B 5/04* (2006.01)
*A61B 5/044* (2006.01)
*A61B 5/06* (2006.01)

(52) U.S. Cl.
CPC ............ *A61B 5/0422* (2013.01); *A61B 5/061* (2013.01); *A61B 5/743* (2013.01); *A61B 5/7282* (2013.01); *A61B 2505/05* (2013.01)

(56) References Cited

U.S. PATENT DOCUMENTS

| | | | |
|---|---|---|---|
| 5,545,204 | A | 8/1996 | Cammilli et al. |
| 5,697,377 | A | 12/1997 | Wittkampf |
| 5,729,129 | A | 3/1998 | Acker |
| 5,913,820 | A | 6/1999 | Bladen et al. |
| 5,983,126 | A | 11/1999 | Wittkampf |
| 6,172,499 | B1 | 1/2001 | Ashe |
| 6,177,792 | B1 | 1/2001 | Govari et al. |
| 6,233,476 | B1 | 5/2001 | Strommer et al. |
| 6,400,139 | B1 | 6/2002 | Khalfin et al. |
| 6,522,907 | B1 | 2/2003 | Bladen et al. |
| 6,574,498 | B1 | 6/2003 | Gilboa |
| 6,690,963 | B2 | 2/2004 | Ben-Haim et al. |
| 6,788,967 | B2 | 9/2004 | Ben-Haim et al. |
| 7,263,397 | B2 | 8/2007 | Hauck et al. |
| 7,536,218 | B2 | 5/2009 | Govari et al. |
| 7,684,850 | B2 | 3/2010 | Govari et al. |
| 7,848,789 | B2 | 12/2010 | Govari et al. |
| 8,046,052 | B2 | 10/2011 | Verard et al. |
| 8,137,343 | B2 | 3/2012 | Harlev et al. |
| 8,167,876 | B2 | 5/2012 | Harlev et al. |
| 8,175,681 | B2 | 5/2012 | Hartmann et al. |
| 8,185,192 | B2 | 5/2012 | Markowitz et al. |
| 8,401,616 | B2 | 3/2013 | Verard et al. |
| 8,401,625 | B2 | 3/2013 | Harlev et al. |
| 8,494,614 | B2 | 7/2013 | Markowitz et al. |
| 9,078,583 | B2 | 7/2015 | Nguyen et al. |
| 9,427,168 | B2 | 8/2016 | Edwards et al. |
| 9,498,143 | B2 | 11/2016 | Edwards et al. |
| 9,763,588 | B2 | 9/2017 | Edwards et al. |
| 2002/0030483 | A1 | 3/2002 | Gilboa |
| 2003/0023130 | A1 | 1/2003 | Ciaccio et al. |
| 2004/0097805 | A1 | 5/2004 | Verard et al. |
| 2005/0033137 | A1 | 2/2005 | Oral et al. |
| 2006/0173269 | A1 | 8/2006 | Glossop |
| 2006/0235476 | A1 | 10/2006 | Gunderson et al. |
| 2007/0016007 | A1 | 1/2007 | Govari et al. |
| 2007/0159488 | A1 | 7/2007 | Danskin et al. |
| 2007/0208260 | A1 | 9/2007 | Afonso |
| 2007/0232949 | A1 | 10/2007 | Saksena |
| 2008/0161681 | A1 | 7/2008 | Hauck |
| 2009/0027403 | A1 | 1/2009 | Jung |
| 2009/0264748 | A1 | 10/2009 | Markowitz et al. |
| 2010/0004550 | A1 | 1/2010 | Ishay et al. |
| 2010/0152571 | A1 | 6/2010 | Hartmann et al. |
| 2010/0168560 | A1* | 7/2010 | Hauck ..................... A61B 5/06 600/424 |
| 2011/0144509 | A1 | 6/2011 | Kahlert et al. |
| 2011/0230775 | A1 | 9/2011 | Barley et al. |
| 2011/0288605 | A1 | 11/2011 | Kaib et al. |
| 2012/0209343 | A1 | 8/2012 | Efimov et al. |
| 2013/0096394 | A1 | 4/2013 | Gupta et al. |
| 2013/0116681 | A1 | 5/2013 | Zhang |
| 2013/0267835 | A1 | 10/2013 | Edwards |
| 2015/0320515 | A1 | 11/2015 | Edwards et al. |

FOREIGN PATENT DOCUMENTS

| | | |
|---|---|---|
| JP | H07-79996 | 3/1995 |
| WO | WO 2012/092016 | 7/2012 |
| WO | WO 2013/123549 A1 | 8/2013 |

OTHER PUBLICATIONS

International Search Report and Written Opinion for International Application No. PCT/US2014/052356, dated Jan. 20, 2015.

Search Report and Written Opinion for International Patent Application No. PCT/US2015/029031, dated Aug. 13, 2015.

Brooks, A. G. et al., "Outcomes of Long-Standing Persistent Atrial Fibrillation Ablation: A Systematic Review," Heart Rhythm, 7(6):835-846 (2010).

Calkins, H. et al., "2012 HRS/EHRA/ECAS Expert Consensus Statement on Catheter and Surgical Ablation of Atrial Fibrillation: Recommendations for Patient Selection, Procedural Techniques, Patient Management and Follow-up, Definitions, Endpoints, and Research Trial Design," Europace, 14:528-590p (2012).

Cuculich, P. S. et al., "Noninvasive Characterization of Epicardial Activation in Humans With Diverse Atrial Fibrillation Patterns," Circulation, 122(14):1364-1372 (2010) and supplemental materials.

Go, A. S. et al., "Prevalence of Diagnosed Atrial Fibrillation in Adults: National Implications for Rhythm Management and Stroke Prevention: the AnTicoagulation and Risk Factors in Atrial Fibrillation (ATRIA) Study," JAMA, 285(18):2370-2375 (2001).

Haissaguerre, M. et al., "Driver Domains in Persistent Atrial Fibrillation," Circulation, 130:530-538 (2014).

Haissaguerre, M. et al., "Spontaneous Initiation of Atrial Fibrillation by Ectopic Beats Originating in the Pulmonary Veins," N. Engl. J. Med., 339(10):659-666 (1998).

Jadidi, A. S. et al., "Inverse Relationship Between Fractionated Electrograms and Atrial Fibrosis in Persistent Atrial Fibrillation: Combined Magnetic Resonance Imaging and High-Density Mapping," Journal of the American College of Cardiology, 62(9):802-812 (2013).

Miller, J. M. et al., "Initial Independent Outcomes From Focal Impulse and Rotor Modulation Ablation for Atrial Fibrillation: Multicenter FIRM Registry," J. Cardiovasc. Electrophysiol., 25(9):921-929 (2014).

Miyasaka, Y. et al., "Secular Trends in Incidence of Atrial Fibrillation in Olmsted County, Minnesota, 1980 to 2000, And Implications on the Projections for Future Prevalence," Circulation, 114(2):119-125 (2006).

Narayan, S. M. et al., "Treatment of Atrial Fibrillation by the Ablation of Localized Sources: Confirm (Conventional Ablation for Atrial Fibrillation With or Without Focal Impulse and Rotor Modulation) Trial," Journal of the American College of Cardiology, 60(7):628-636 (2012).

Narayan, S. M. et al., "Computational Mapping Identifies Localized Mechanisms for Ablation of Atrial Fibrillation," PLos ONE, 7(9):e46034 (2012), 8 pages.

Pandit, S. V. et al., "Rotors and the Dynamics of Cardiac Fibrillation," Circulation Research, 112(5):849-862 (2013).

Wilber, D. J. et al., "Comparison of Antiarrhythmic Drug Therapy and Radiofrequency Catheter Ablation in Patients With Paroxysmal Atrial Fibrillation: A Randomized Controlled Trial," JAMA, 303(4):333-340 (2010).

Kurian, Thomas et al., "Identification of drivers in patients with persistent atrial fibrillation using a novel spatiotemporal computational algorithm integrated with electroanatomic mapping," Abstract, The Boston AF Symposium, Apr. 9, 2014 pp. 564-565.

Karthikeyan, Umapathy et al., "Phase Mapping of Cardiac Fibrillation," Circ Arrhythm Electrophysiol, 2010; 3:105-114.

Kremen, V. et al., "Comparison of Several Classifiers to Evaluate Endocardial Electrograms Fractionation in Human," 31st Annual International Conference of the IEEE EMBS, Sep. 2009; 2502-2505.

(56) References Cited

OTHER PUBLICATIONS

Extended European Search Report issued by the European Patent Office for Application No. 14837118.0, dated Mar. 17, 2017, 9 pages.

Extended European Search Report issued by the European Patent Office for Application No. 15788895.9, dated Jan. 2, 2018, 8 pages.

Ghoraani, B., et al., "Localized rotational activation in the left atrium during human atrial fibrillation: Relationship to complex fractionated atrial electrograms and low-voltage zones," Heart Rhythm 10(12):1830-1838.

* cited by examiner

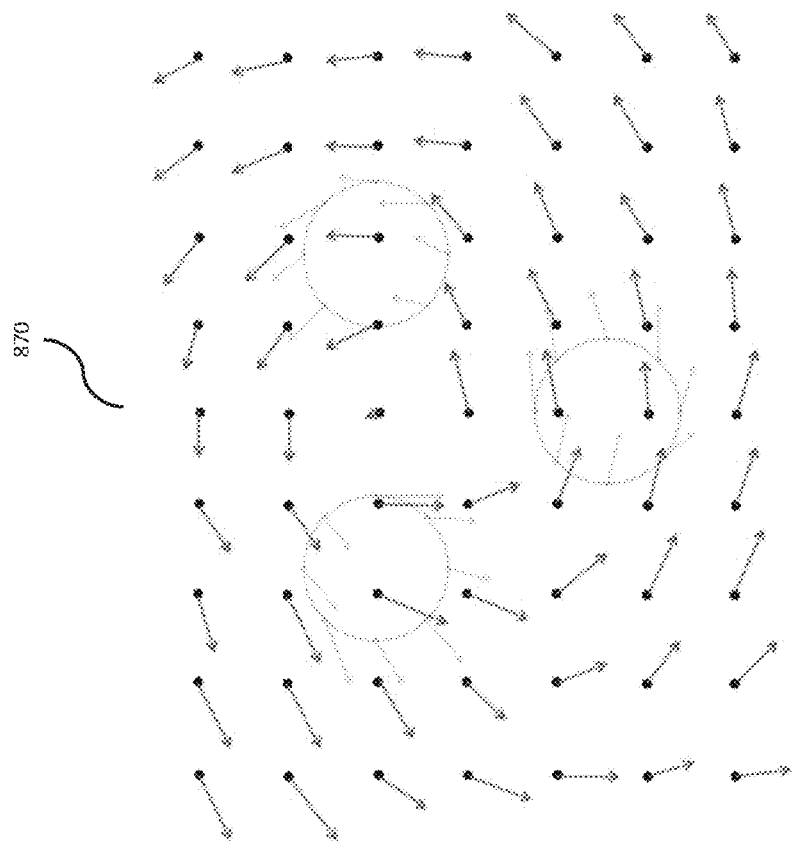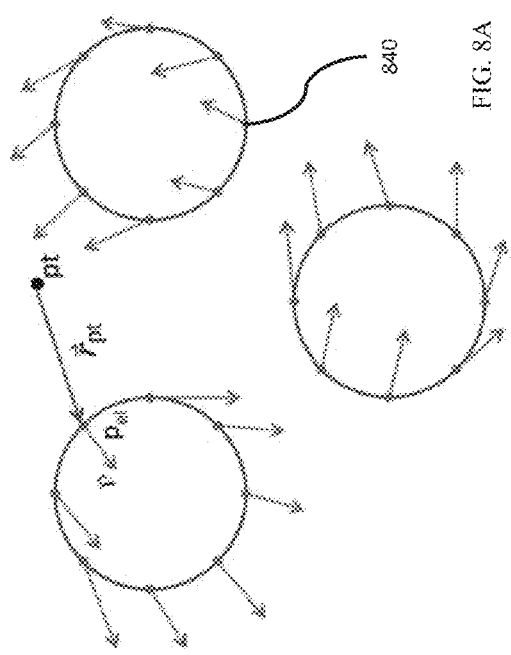
FIG. 8C
FIG. 8A
$$\vec{r}_{pt} = p_t - p_{el}$$
$$d = \|\vec{r}_{pt}\|$$
$$\hat{v}_{pt} = \frac{\sum_n^N v_n \left(\frac{1}{d_n}\right)}{N}$$
$$v_{pt} = \frac{\sum_n^N \|\vec{v}_{p,n}\| \left(1 - \frac{d_n}{d_{total}}\right)}{N-1}$$
$$d_{total} = \sum_n^N d_n$$
FIG. 8B

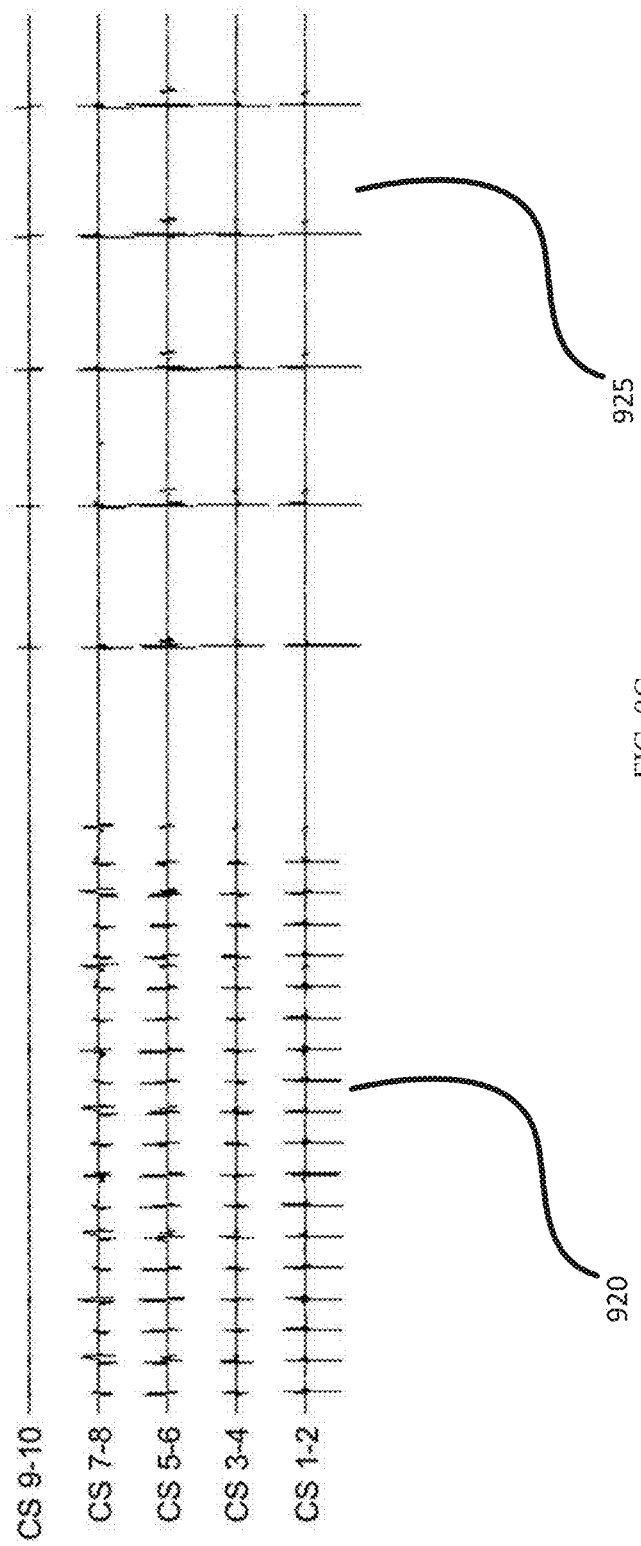

METHODS, SYSTEMS, AND APPARATUS FOR IDENTIFICATION AND CHARACTERIZATION OF ROTORS ASSOCIATED WITH ATRIAL FIBRILLATION

CROSS-REFERENCE TO RELATED APPLICATIONS

This application is a continuation of U.S. patent application Ser. No. 14/737,116, filed Jun. 11, 2015, entitled "Methods, Systems, and Apparatus for Identification and Characterization of Rotors Associated with Atrial Fibrillation," now U.S. Pat. No. 9,498,143, which is a continuation of U.S. patent application Ser. No. 14/466,588, filed Aug. 22, 2014, entitled "Methods, Systems, and Apparatus for Identification and Characterization of Rotors Associated with Atrial Fibrillation," now U.S. Pat. No. 9,078,583, each of which is incorporated herein by reference in its entirety. U.S. patent application Ser. No. 14/466,588, now U.S. Pat. No. 9,078,583, claims priority to and the benefit of U.S. Provisional Patent Application No. 61/868,950, filed Aug. 22, 2013, and entitled "Method and Apparatus to Create 4-Dimensional Maps of Atrial Fibrillation Focal Drivers," and U.S. Provisional Patent Application No. 61/988,651, filed May 5, 2014, and entitled "Methods, Systems, and Apparatus for Identification and Characterization of Rotors Associated with Fibrillation," each of which is incorporated herein by reference in its entirety.

BACKGROUND

The invention relates generally to methods, systems, and apparatus for identifying and characterizing rotors associated with heart arrhythmias such as atrial fibrillation. Some methods described herein are suitable for classifying rotors as substrate rotors, which may significantly influence arrhythmias, and non-substrate rotors, which may not strongly influence arrhythmias.

In the last few years, scientific understanding of atrial fibrillation has discovered that the electrical activity in the heart during atrial fibrillation is not complete chaos as was once accepted under the Moe model of random wavelets of electrical activity causing atrial fibrillation. Rather, there are local organized electrical drivers of atrial fibrillation. Recent research has revealed that electrical patterns in the heart, commonly referred to as rotors, play an important role in many cases of fibrillation, particularly persistent atrial fibrillation. Currently, surgical systems are available that modify cardiac tissue during treatment using RF energy, cryo, laser, direct current (DC), stem-cells, or drugs. In some situations modifying, ablating, or "burning" a rotor can significantly improve cardiac function by returning the patient to normal sinus heartbeat rhythm.

Known surgical techniques, however, have inconsistent results; ablation of some rotors results in significant changes in heart rhythm, while ablation of other rotors does not have a significant effect. Current medical equipment and techniques cannot identify which rotors will have a significant effect if ablated. A need therefore exists for methods, systems, and apparatus for identifying and characterizing rotors. Furthermore, a targeted approach to treating rotors in atrial fibrillation patients will shorten treatment procedure times, reduce cost of procedures, reduce the need for repeat procedures, preserve heart tissue, and enable patients to live longer and fuller lives.

SUMMARY OF THE INVENTION

In some embodiments, a system includes a near-field instrument to be placed inside a chamber of a heart, a far-field instrument to be placed in a stable position in relation to the heart (e.g., the coronary sinus), and a control unit. The control unit is configured to receive position coordinates of the near-field instrument and electrogram information from the far-field instrument. The control unit is configured to identify a unique pattern in the electrogram information from the far-field instrument. When the unique pattern is detected, the control unit is configured to receive electrogram information from the near-field instrument and store the associated near-field instrument position information with the unique pattern information and near-field instrument electrogram information. Upon moving the near-field instrument within the heart chamber, the control unit is configured to identify the unique pattern in the electrogram information from the far-field instrument again. Upon detecting the unique pattern, the control unit is configured to receive electrogram information from the near-field instrument at the new position and store the associated new near-field instrument position information with the unique pattern information and near-field instrument electrogram information. While recording electrogram information from the near-field instrument, the control unit is also configured to receive voltage and complex fractionated atrial electrogram (CFAE) characteristics of the tissue from the near-field instrument. This information combined with rotor information can be used to determine substrate versus non-substrate rotor characteristics.

BRIEF DESCRIPTION OF THE DRAWINGS

FIGS. 8A-8C are depictions of conduction vectors and the calculations that allow interpolation of conduction vectors throughout a region of the heart based on actual measured conduction vectors, according to an embodiment.

FIG. 9C depicts the electrical activity of a heart in fibrillation prior to an ablation at a substrate rotor site and the electrical activity of the heart in normal sinus rhythm just after the ablation at the substrate rotor site, according to an embodiment.

DETAILED DESCRIPTION

In some embodiments, a system includes a near-field instrument to be placed inside a chamber of a heart, a far-field instrument to be placed in a stable position in relation to the heart (e.g., the coronary sinus), and a control unit. The control unit is configured to receive position coordinates of the near-field instrument and electrogram information from the far-field instrument. The control unit is configured to identify a unique pattern in the electrogram information from the far-field instrument. When the unique pattern is detected, the control unit is configured to receive electrogram information from the near-field instrument and store the associated near-field instrument position information with the unique pattern information and near-field instrument electrogram information. Upon moving the near-field instrument within the heart chamber, the control unit is configured to identify the unique pattern in the electrogram information from the far-field instrument again. Upon detecting the unique pattern, the control unit is configured to receive electrogram information from the near-field instrument at the new position and store the associated new near-field instrument position information with the unique pattern information and the near-field instrument electrogram information associated with the new position.

In some embodiments, a method includes receiving position coordinates of a near-field instrument from within a patient's heart chamber and electrogram information from a far-field instrument that is located at a stable position with respect to the patient's heart. The method further includes identifying a pattern in the far-field electrogram data, capturing electrogram data from the near-field instrument when the pattern is detected in the far-field electrogram data, and associating in memory the position coordinates and electrogram data of the near-field instrument and the identified pattern. The method further includes moving the position of the near-field instrument within the patient's heart chamber and repeating the steps to gather near-field electrogram data at the new position when the pattern is identified in the electrogram data of the far-field instrument.

In some embodiments, a method including identifying the location of one or more rotors (i.e., spiraling conduction vector patterns) in a patient's heart. Once the locations are identified, determining the stability of each of the rotors, measuring voltage characteristics and complex fractionation characteristics of the heart tissue in and around the rotor location, and using the stability information and characteristic information to identify which rotors are sources of arrhythmia.

As used herein, the singular forms "a," "an," and "the" include plural referents unless the context clearly dictates otherwise. Thus, for example, the term "an electrode" is intended to mean a single electrode or a combination of electrodes.

Figure 1:
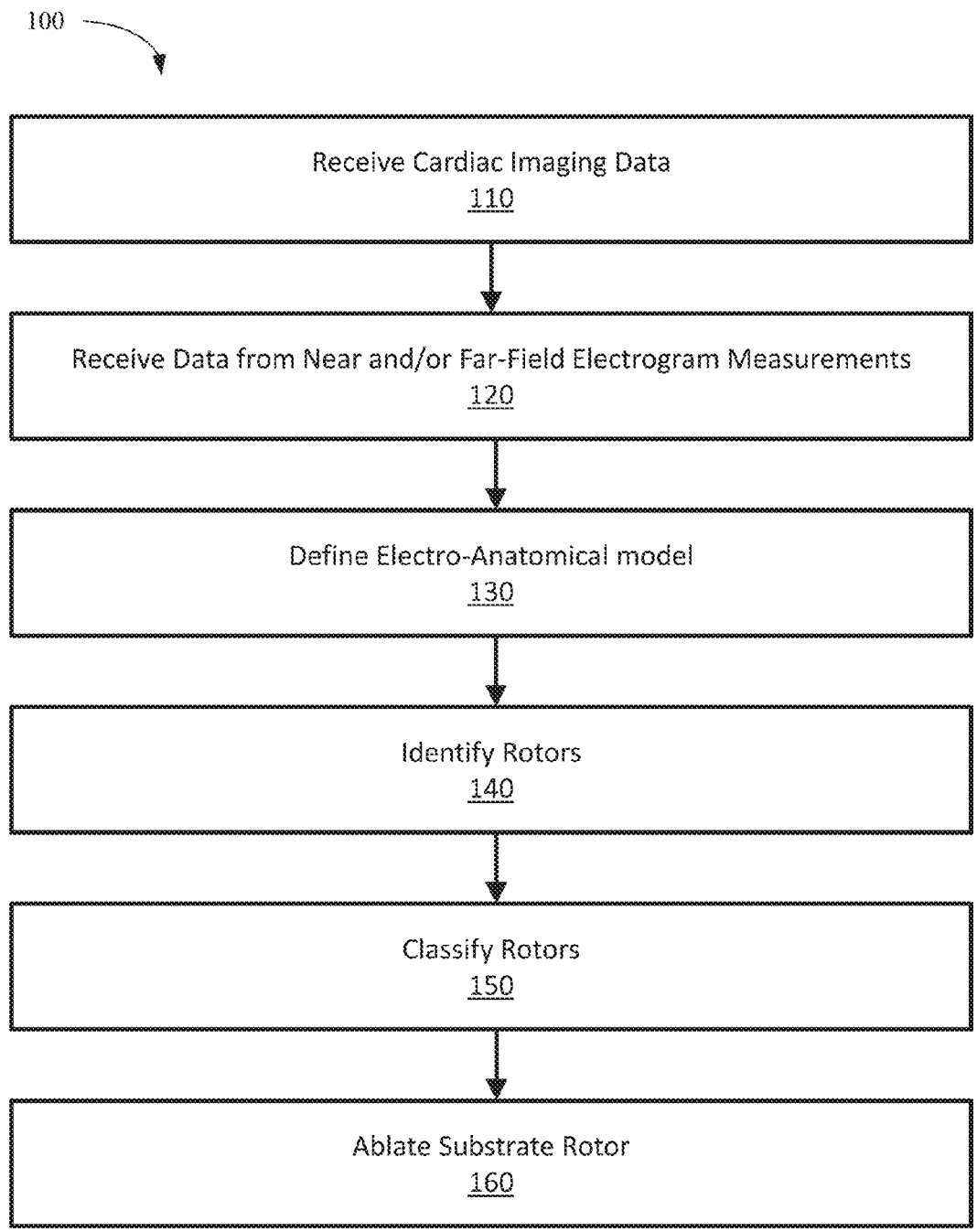
FIG. 1 is a flow chart of a method of treating a cardiac arrhythmia, according to an embodiment.

FIG. 1 illustrates a flow chart of a method 100 of treating a cardiac arrhythmia. At 110, a control unit can receive cardiac imaging data. The cardiac imaging data, also commonly referred to as an electro-anatomical map, a three-dimensional (3D) heart geometry, or a geometry, can be data created from a cluster of 3D points created by tracking an instrument inside the heart as it is used to paint the interior surface of a chamber or from applying edge detection algorithms to computerized tomography (CT) scan, magnetic resonance imaging (MRI), ultrasound, x-ray, and/or any other suitable imaging technology to identify heart wall surfaces. In some embodiments, the imaging data can be suitable to generate, define, and/or render a 3D model of the heart, for example, using various linear and non-linear 3D registration techniques. In some embodiments, the imaging data can include time data such that a four-dimensional (4D) model of the heart can be generated, defined, and/or rendered. For example, a video, real-time, and/or animated model of the heart can be created using the cardiac imaging data.

At 120, a control unit can receive near- and/or far-field cardiac electrogram (EGM) data. For example, a near-field measurement instrument can be used to measure a patient's heart signal. The near-field measurement instrument can be an instrument having one or more electrodes, such as the instrument depicted in FIG. 10 and described in more detail herein. For example, the near-field instrument can be a loop catheter with electrodes, a basket catheter with electrodes that is designed to fill a heart chamber, a basket catheter with electrodes that is designed to partially fill a heart chamber, a star shaped catheter with electrodes, or any another suitable multi-electrode catheter capable of sensing cardiac electrical activity. In some embodiments, the near-field measurement instrument can be the antenna catheter instrument described with respect to FIG. 10.

In some embodiments, the near-field measurement instrument can have an electromagnetic sensor integrated into it such that the near-field measurement instrument can be localized by a tracking system. In some embodiments, the near-field measurement instrument can be localized by tracking systems that utilize electromagnetic, electropotential, impedance, or any other suitable technology for tracking. For example, the tracking system can be the tracking system disclosed in U.S. patent application Ser. No. 13/747,266 to Edwards, filed on Jan. 22, 2013, now U.S. Pat. No. 9,510,772, entitled "System and Methods for Localizing Medical Instruments During Cardiovascular Medical Procedures," which is incorporated by reference herein in its entirety.

In some embodiments, the near-field measurement instrument can be placed within a chamber of a patient's heart for measuring the patient's heart signal and capturing electromagnetic positional information. The instrument can be moved within the chamber of the patient's heart to capture positional and electrogram data at multiple locations within the chamber of the patient's heart as described in more detail herein with respect to FIG. 11.

In some embodiments, a far-field measurement instrument can be used to measure a patient's heart signal from a distance. The far-field measurement instrument can be, for example, a coronary sinus catheter capable of sensing cardiac electrogram activity, such as the instrument depicted in FIG. 10 and described in more detail herein. For another example, a far-field measurement instrument can be multiple electrodes placed on the body surface of the patient with the capability of sensing cardiac electrical activity from a distance. In some embodiments, the far-field measurement instrument can have an electromagnetic sensor integrated into it such that the far-field measurement instrument can be localized by a positional tracking system. For example, the far-field measurement instrument can be localized by tracking systems that utilize electromagnetic, electropotential, impedance, or any other suitable technology for tracking the location of the instrument with respect to the patient's heart. The tracking system can be, for example, the tracking system disclosed in U.S. patent application Ser. No. 13/747, 266 as described above.

In some embodiments, the far-field instrument can be placed in relation to the patent's heart such that it is in a stable location. For example, a coronary sinus catheter can be placed within the coronary sinus of the patent's heart, which is a stable location with respect to the patient's heart. In other words, the far-field instrument can be an instrument that does not move with respect to the patient's heart during the course of the patient's cardiac arrhythmia treatment. In some embodiments, the far-field instrument can be placed more specifically in a stable location with respect to the patient's left atrium where sources of atrial fibrillation tend to be found.

Figure 11:
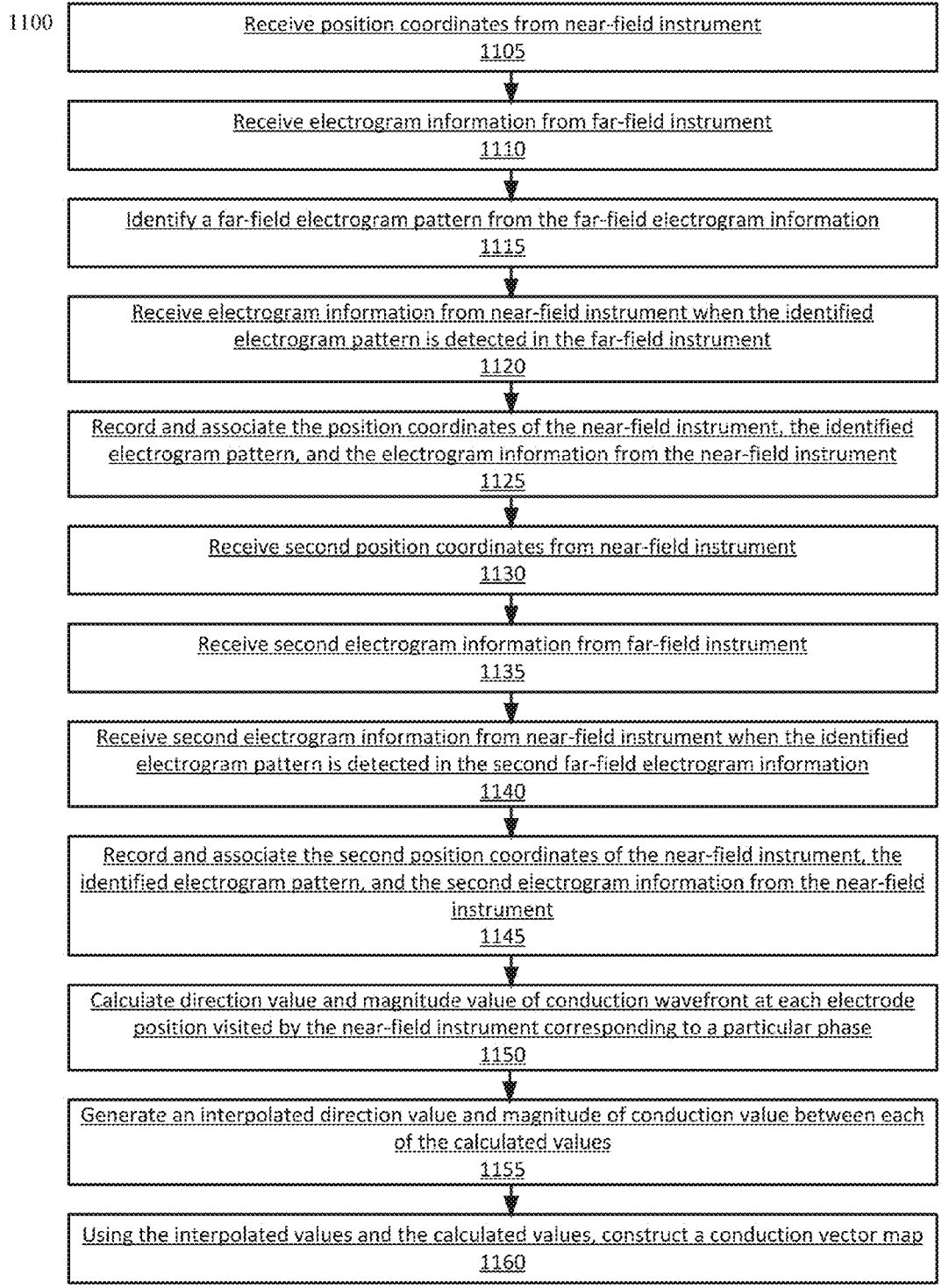
FIG. 11 is a flow chart of a method of constructing a conduction vector map, according to an embodiment.

The near-field measurement instrument can capture data at various locations and positional data in X-Y-Z space, which can be sent to and received by a control unit for processing as described in further detail herein with respect to FIG. 11. The near-field measurement data can be stored in a computer memory, including RAM, ROM, flash drive, external hard drive, or any other suitable memory device. The data can be configured to be stored in a database, lookup table, and/or any other suitable configuration for storing data, such as, for example, as described in further detail herein with respect to FIG. 7. Furthermore, the far-field measurement instrument can capture data associated with each near-field measured point. The far-field data can be stored in a computer memory, including RAM, ROM, flash drive, external hard drive, or any other suitable memory device. The data can be configured to be stored in a database, lookup table, and/or any other suitable configuration for storing data. The capture and storage of data from the far-field instrument and the near-field instrument will be described in further detail herein with respect to FIGS. 5 and 11.

Figure 2A:
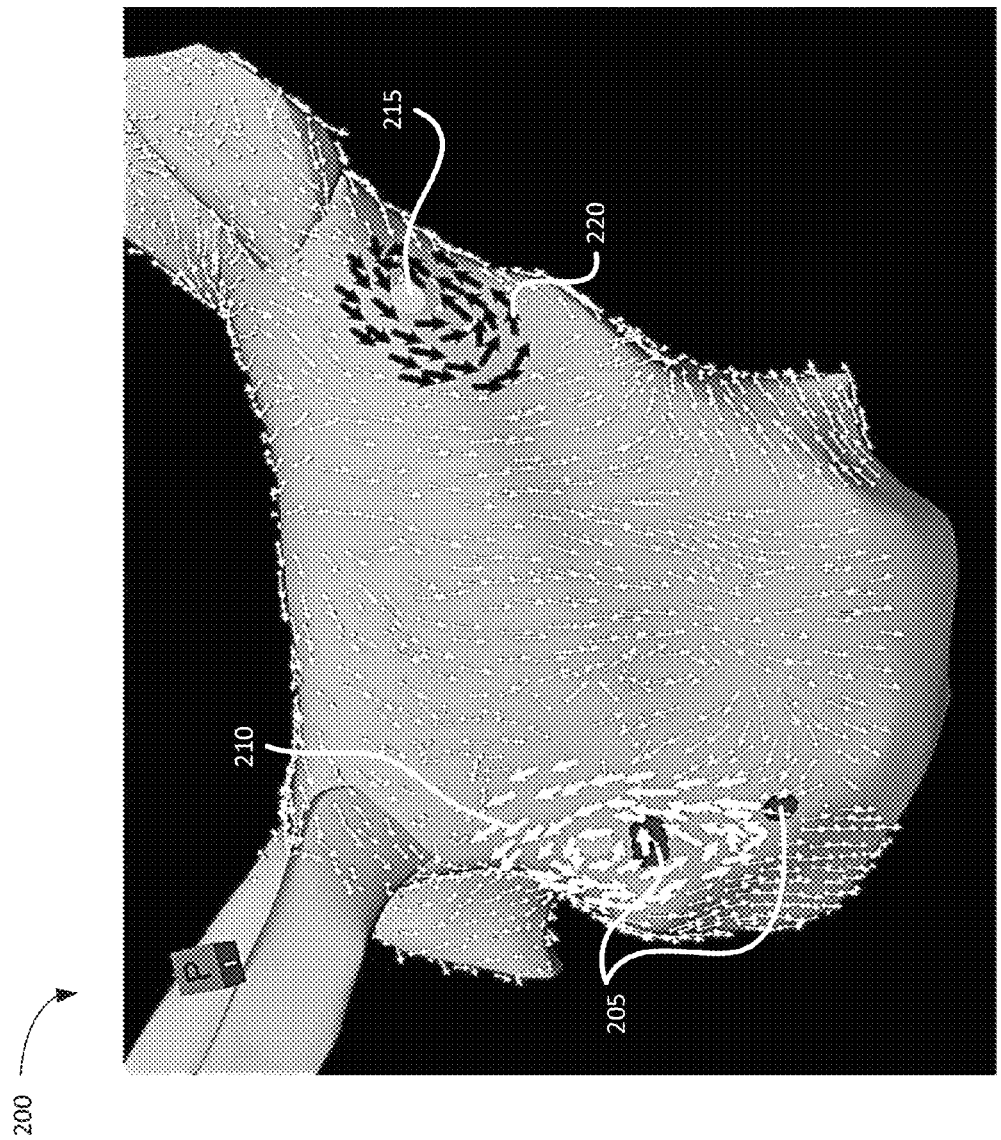
FIGS. 2A and 2B depict electro-anatomical models of a left atrium showing cardiac electrical conduction patterns in two unique phases, according to an embodiment.
Figure 2B:
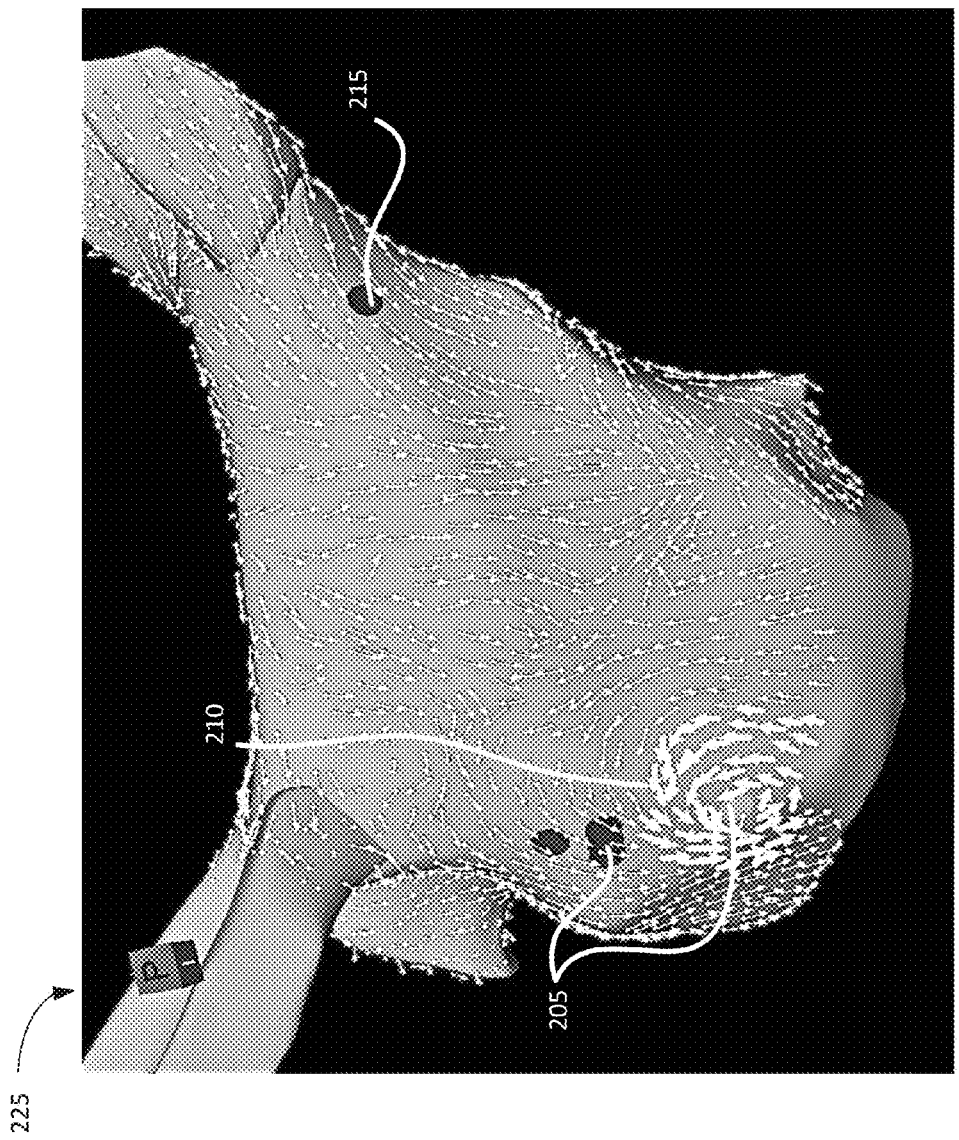

At 130, the electrogram data received at 120 and the imaging data received at 110 can be combined or integrated to define an electro-anatomical model, such as the model of FIG. 2A or FIG. 2B. Specifically, FIG. 2A represents one phase of atrial fibrillation corresponding to one pattern detected on the far-field instrument and FIG. 2B represents a second phase of atrial fibrillation corresponding to a second pattern detected on the far-field instrument. The electro-anatomical model can be a 3D or 4-dimensional (4D) model of a heart, or a portion thereof, including a visualization (e.g., a vector field, heat map, and/or any other suitable visualization) of electric potentials, conduction patterns, velocities, and/or any other suitable electro-anatomic feature, such as, for example, CFAE mapping.

The electro-anatomical models can be constructed using a control unit that can be configured to find patterns on the far-field data and index near-field cardiac electrical data and near-field instrument position location information to far-field data patterns. The control unit can organize a set of near-field cardiac electrical data from multiple near-field position locations that display the same far-field data patterns as described in more detail with respect to FIGS. 5 and 11. The control unit can use this set of data and various interpolation techniques to generate a 3D map of electrical activity for a region of the heart corresponding to that far-field data pattern. This process can be repeated for multiple far-field data patterns to create multiple maps. These multiple maps can correspond to different repeating phases of atrial fibrillation as detected by the patterns in the far-field data. As described in more detail herein, these multiple maps can be sequenced to create a composite 4D map of an arrhythmia such as atrial fibrillation over time.

As an example of the 3D mapping, FIGS. 2A and 2B depict 3D left atrial electro-anatomical models of a human heart. Electro-anatomical models 200 and 225 depict the left atrium of the heart during two separate phases of atrial fibrillation. Further, electro-anatomical models 200 and 225 each show cardiac conduction patterns during its respective phase. As seen in electro-anatomical models 200 and 225, the conduction patterns can be used to identify contraction of heart muscle. Contraction of heart muscle can sometimes be seen within the electro-anatomical model as conduction patterns that appear to swirl or form a circular pattern. The swirling conduction patterns can be used to identify rotors within the heart tissue.

At 140, the electro-anatomical model can be used to identify rotors. Rotors can be identified by any suitable technique. For example, with respect to FIG. 2A, within electro-anatomical model 200, two locations of swirling conduction vectors 210, 220 can be identified. The thick, white arrows that form a circular or swirling pattern 210 can be used to identify the substrate based rotor 205. The thick, black arrows that form a circular or swirling pattern 220 can be used to identify the non-substrate based rotor 215. Note that, as described in more detail herein with respect to FIG. 4, the substrate based rotor 205 is present in multiple phases of conduction as depicted in FIG. 2A and FIG. 2B and is thereby more stable than the non-substrate based rotor 215 that is only present in one phase of conduction as depicted in FIGS. 2A and 2B. With only a single electro-anatomical model, the rotor locations 205 and 215 can be identified, but the rotors cannot be classified as substrate based or non-substrate based without more information.

Stated differently, rotors can be identified, in some embodiments, using a computational mapping algorithm to, for example, integrate spatiotemporal wave front patterns during atrial fibrillation on the electro-anatomical model defined at 130. For example, the computational mapping algorithm can search the surface of the electro-anatomical model defined at 130 for complete rotation of conduction velocity vectors. In some embodiments, the complete surface of the model can be searched and one or more rotors can be identified. In some embodiments, when a rotor is identified, the region of rotation associated with the rotor can be searched for additional rotations (e.g., partial and/or complete rotations), for example, over multiple phases. In some embodiments, in addition to or instead of identifying regions of rotation from the electro-anatomical model, voltage transition zones in the underlying tissue can be located and identified by the near-field instrument during data capture, for example, within a region of rotation. In some embodiments, multiple rotors can be associated with a voltage transition zone within a region of rotation. In fact, these tissue voltage transition zones can act like high pressure and low pressure bordering weather patterns that create tornados in nature. In some embodiments, information such as rotor phase percentage, change in voltage between the rotor and an adjacent region, and/or degree of complex fractionation for the region containing the rotor can be calculated and/or determined for each rotor. All of this data can be gathered by the control unit during near-field instrument data sampling at various positions within the heart.

At 150, further information can be used to classify the rotors as substrate based or non-substrate based. An example of a process for using the information to classify rotors will be described in more detail herein with respect to FIG. 4. In some embodiments, the swirling conduction patterns in addition to other information including the stability of the swirling conduction patterns, the voltage of the heart tissue near the swirling conduction patterns, and the complex fractionation of the heart tissue near the swirling conduction patterns can be used to identify which locations within the heart can be causing arrhythmia. Where the information indicates a cause of arrhythmia, the swirling conduction patterns can be used to identify a substrate based rotor location. Where the information indicates that the location is not a true cause of arrhythmia, the swirling conduction patterns can be used to identify a non-substrate based rotor location. Stated differently, rotors that are classified as substrate rotors can be associated with causing and/or driving arrhythmias, while rotors that are classified as non-substrate rotors may not be associated with a true arrhythmia cause and may simply be the result of electrical wavefront collisions.

As will be described in further detail herein, the substrate based rotor 205, partially characterized by the swirling conduction pattern 210, is indicated in the phase depicted in electro-anatomical model 200 as well as in the phase depicted in electro-anatomical model 250. The non-substrate based rotor 215 is shown in electro-anatomical model 200 characterized by the swirling conduction pattern 220. The swirling conduction pattern 220 does not appear in electro-anatomical model 225, indicating that the rotor 215 is a non-substrate based rotor because it is unstable. Where a rotor is stable, the swirling conduction pattern will appear in electro-anatomical models of multiple phases. Phases will be described in more detail herein with respect to FIG. 11.

Figure 2C:
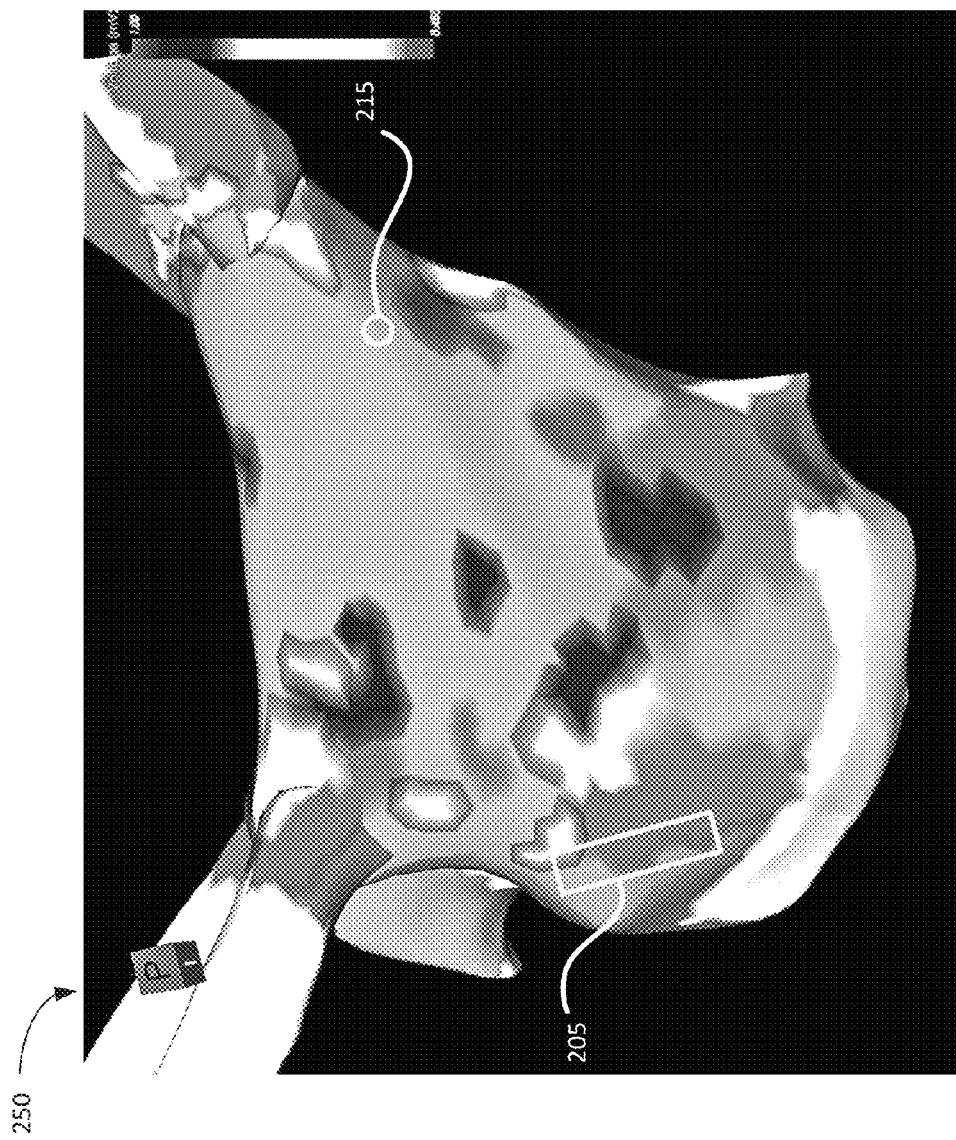
FIG. 2C depicts an electro-anatomical model of the left atrium of FIGS. 2A and 2B showing a map of the voltage characteristics of the underlying tissue, according to an embodiment.

FIG. 2C depicts the left atrium of FIGS. 2A and 2B showing a voltage map 250 of the left atrium. The voltage map 250 highlights areas of healthy tissue (i.e., high voltage) versus scar or unhealthy tissue (i.e., low voltage). While difficult to see in the grey-scale depiction of FIG. 2C, the area around non-substrate based rotor 215 is homogeneous in voltage. Contrastingly, the area around substrate based rotor 205 is heterogeneous in voltage, or a border zone of healthy and scar tissue. In fact, the substrate based rotor 205 appears to migrate along a voltage transition zone over multiple phases of atrial fibrillation much like a tornado would form and move along a high pressure and low pressure weather border zone in nature.

Figure 2D:
FIG. 2D depicts an electro-anatomical model of the left atrium of FIGS. 2A-2C showing a map of the complex fractionation characteristics of the underlying tissue, according to an embodiment.

FIG. 2D depicts the left atrium of FIGS. 2A-2C with a complex fractionated atrial electrogram map (CFAE) 275. The CFAE map 275 highlights areas having noisy fractionation of electrograms (EGMs) versus areas with less fractionation of EGMs. While difficult to see in the grey-scale depiction of FIG. 2D, the area around non-substrate based rotor 215 has noisy fractionation of EGMs, indicating a non-substrate based rotor. The area around substrate based rotor 205 has less fractionation of EGMs, indicating a substrate based rotor. Fractionation can be associated with electrical wavefronts colliding rather than tissue causing or driving an arrhythmia.

Figure 3A:
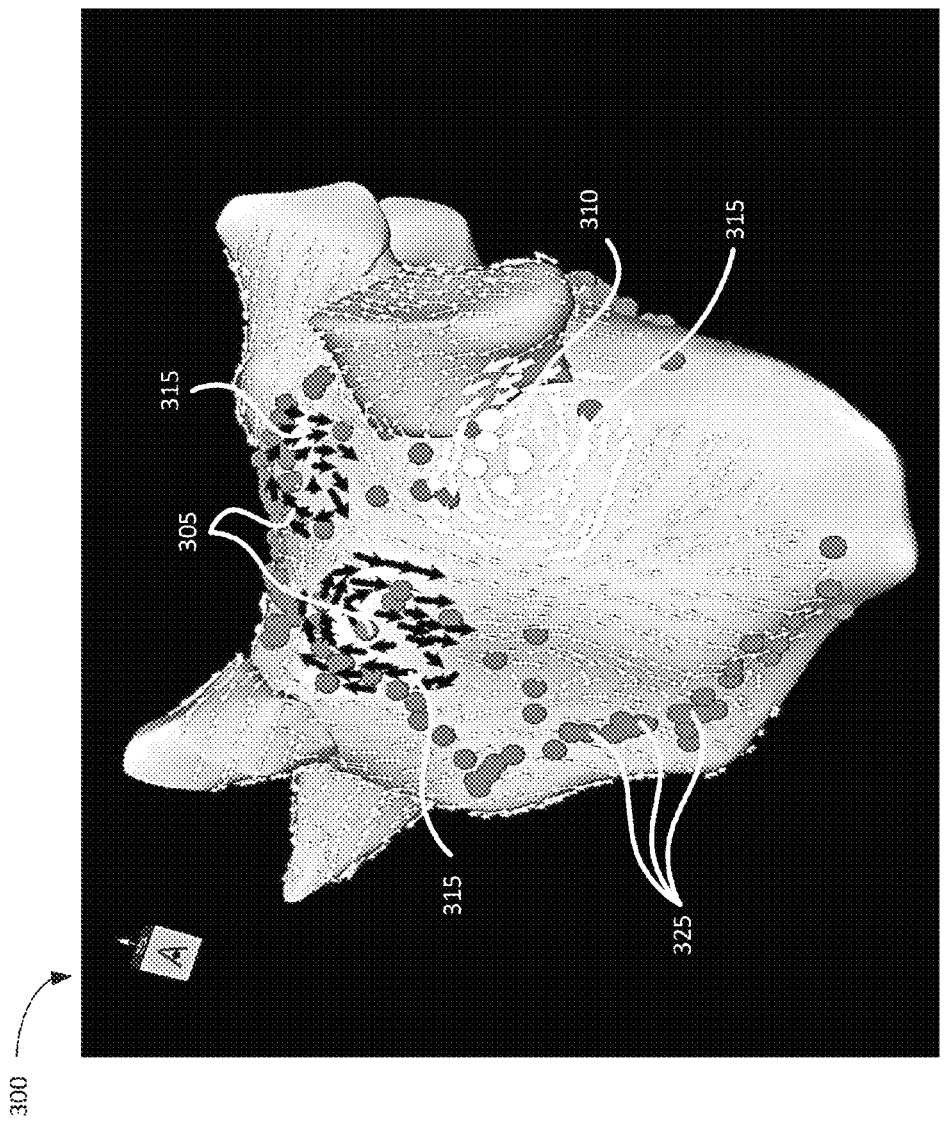
FIG. 3A depicts an electro-anatomical model of a left atrium showing conduction patterns and sites where tissue was burned or ablated in the patient, according to an embodiment.

As another example of an electro-anatomical model, FIG. 3A is an electro-anatomical model 300 of a left atrium showing cardiac conduction patterns. Electro-anatomical model 300 depicts two non-substrate based rotors 305 and one substrate based rotor 310 characterized by swirling conduction vectors 315.

Figure 3B:
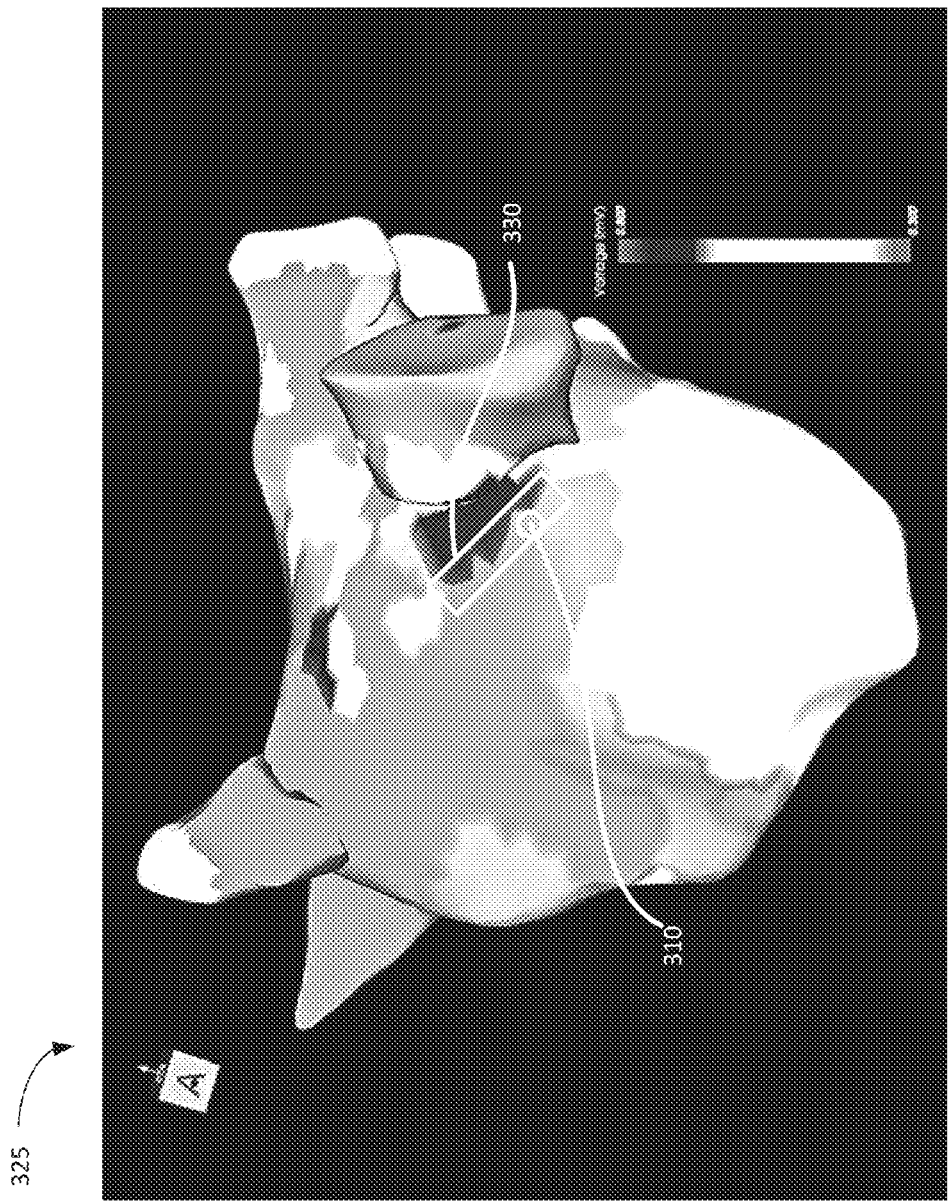
FIG. 3B depicts an electro-anatomical model of the left atrium of FIG. 3A showing a voltage map, according to an embodiment.

As another example of a voltage map, FIG. 3B depicts voltage map 325. Voltage map 325 depicts the left atrium of FIG. 3A, highlighting borders of healthy tissue meeting scar or dead tissue resulting in high voltage transition deltas. As described in further detail herein, the presence of rotor 310 in a voltage transition region 330 is indicative of rotor 310 being a substrate based rotor. Treatment (i.e., ablation) of the non-substrate based rotors 325 for this patient did not improve cardiac rhythm. Treatment of the substrate-based rotor 310 resulted in significant improvements in heart rhythm for this patient.

Figure 9A:
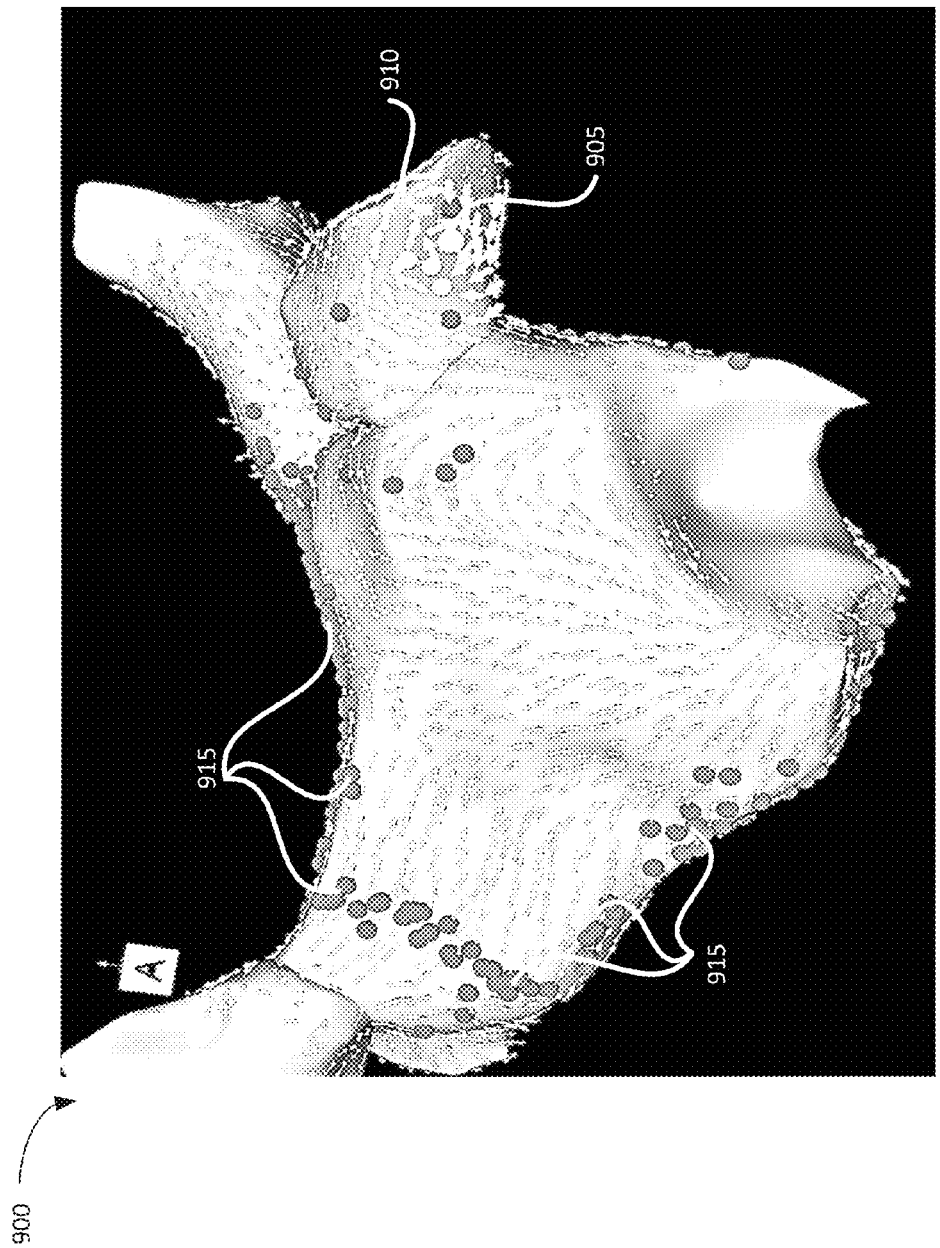
FIG. 9A illustrates the identification and ablation of a substrate based rotor in the left atrium, according to an embodiment.
Figure 9B:
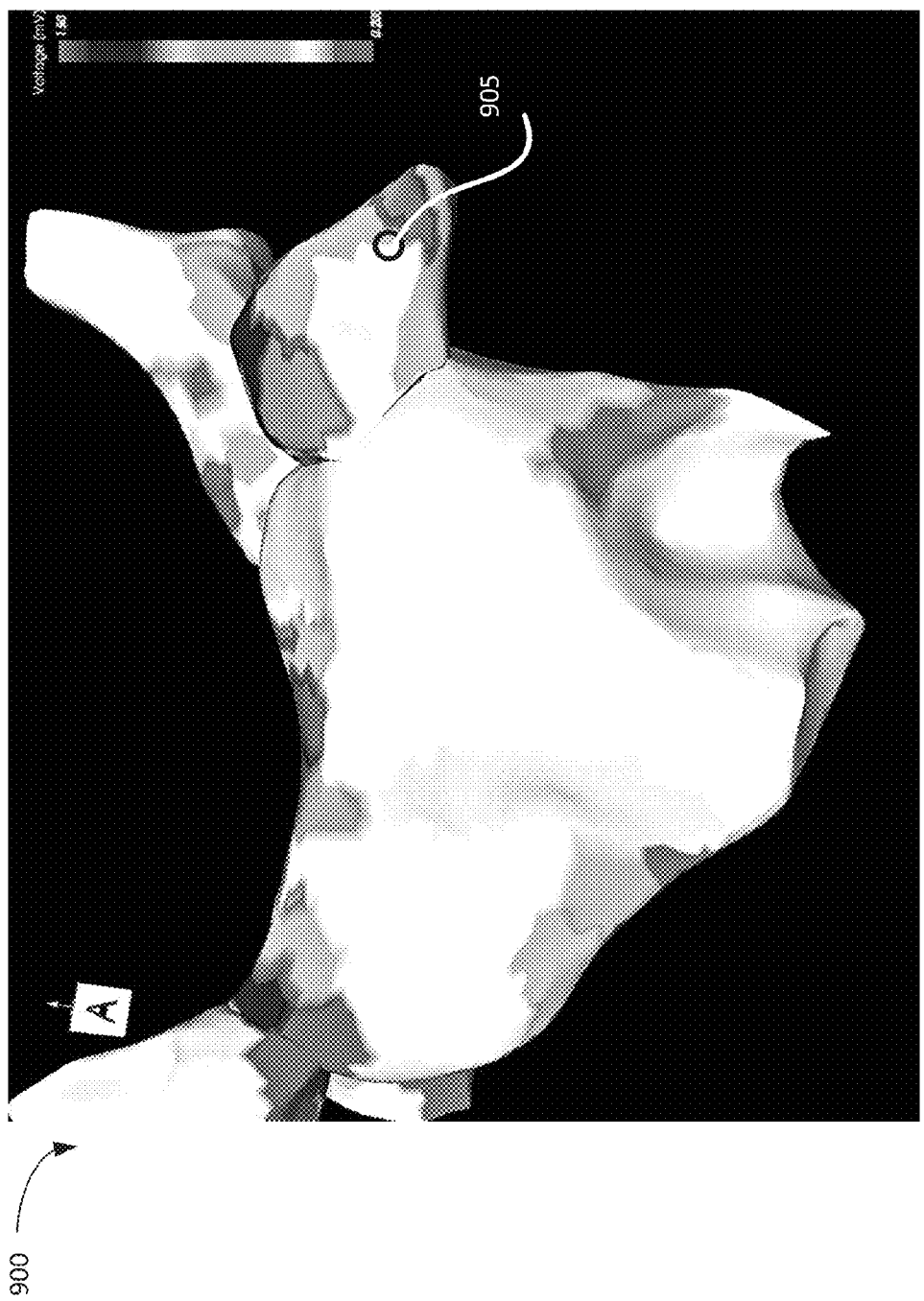
FIG. 9B illustrates a voltage map of the left atrium where a substrate based rotor was identified, according to an embodiment.

Similarly, FIG. 9A depicts an electro-anatomical model 900 showing a substrate based rotor 905 characterized by swirling conduction pattern 910 within the left atrial appendage. FIG. 9B depicts a voltage map that further confirms rotor 905 is a substrate based rotor as it is in an area of high voltage heterogeneity. FIG. 9C is an EKG readout of the heartbeat of the patient belonging to the heart in FIGS. 9A and 9B. When the rotor 905 was ablated, atrial fibrillation as seen in the EKG at 920 converted into normal sinus rhythm at 925. Ablation at other locations 915 (FIG. 9A) produced no such rhythm change in the patient's heartbeat.

As mentioned above, at 160, the rotors classified as substrate rotors can be treated (e.g., ablated or burned) to improve cardiac activity in the patient. Treatment can be performed by known tools and instruments within the field. For example, an ablation catheter can be used to burn the heart tissue near the substrate based rotor. The ablation catheter can be tracked and monitored using a tracking system such as, for example, the tracking system disclosed in U.S. patent application Ser. No. 13/747,266 as described above. Treatment of substrate rotors, at 160, is strongly correlated with improved cardiac rhythms. Non-substrate rotors may not be treated, at 160. Treatment of non-substrate rotors is not correlated with, or is only weakly correlated with improved cardiac rhythms. In an embodiment where only substrate rotors are treated, treatment time can be reduced and/or more cardiac tissue can be preserved as compared to an embodiment where substrate and non-substrate rotors are treated.

Figure 4:
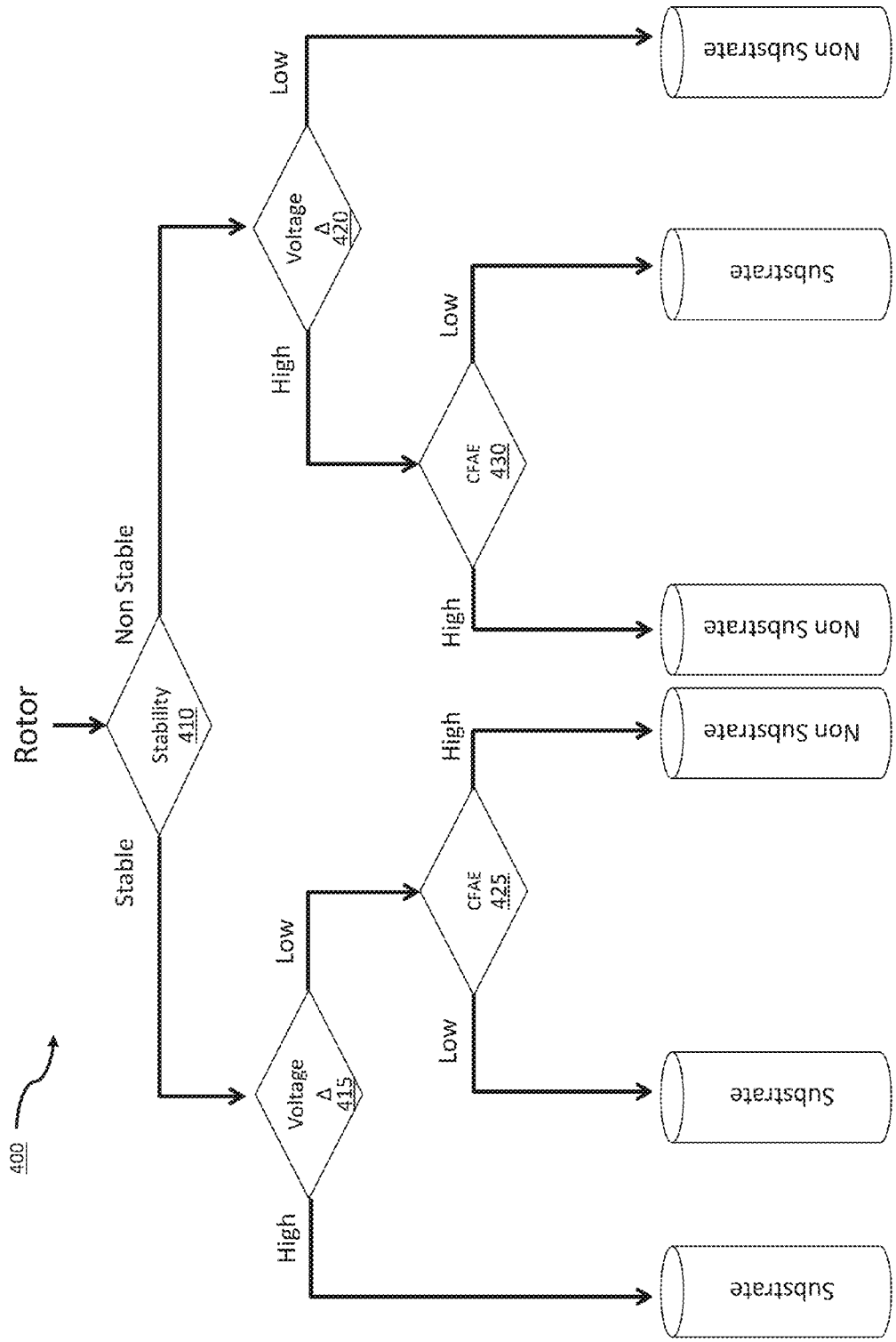
FIG. 4 is a flow chart of a method for classifying rotors, according to an embodiment.
Figure 5A:
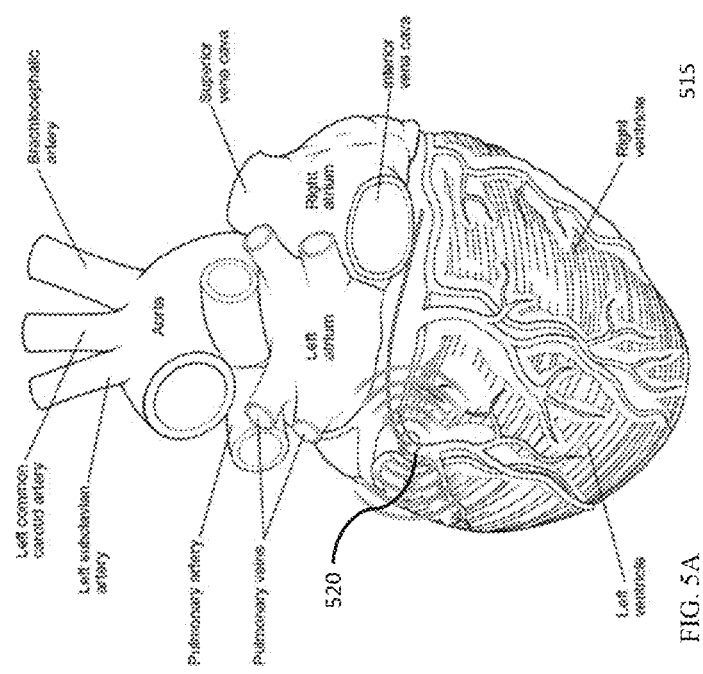
FIG. 5A illustrates a human heart having a multi-electrode catheter instrument located in the coronary sinus, according to an embodiment.
Figure 5B:
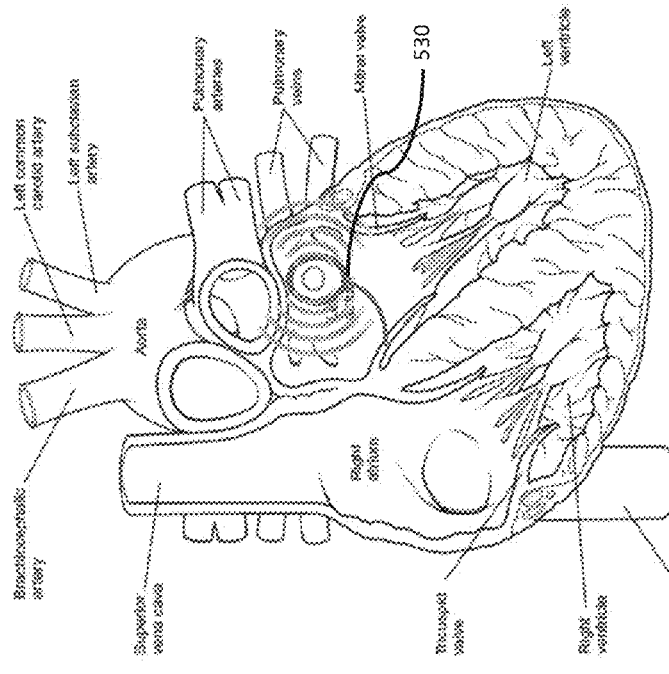
FIG. 5B illustrates a human heart having a multi-electrode catheter instrument with electrodes located in the left atrium, according to an embodiment.
Figure 5C:
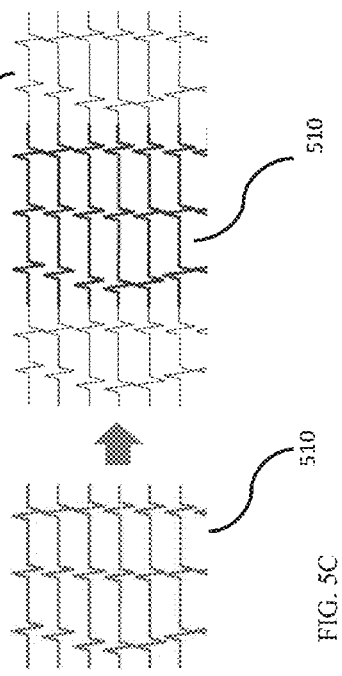
FIG. 5C illustrates a pattern template of electrogram data, according to an embodiment.
Figure 5D:
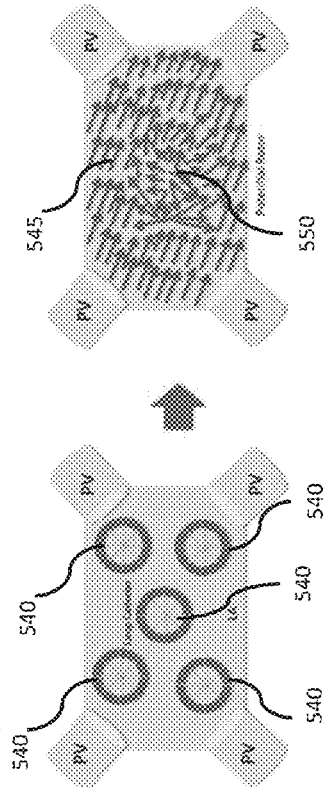
FIG. 5D illustrates measured conduction vectors in a left atrium, according to an embodiment.

Turning now to FIG. 4, it is a decision tree 400 for classifying rotors. In some embodiments, this decision tree can be used at 150 (FIG. 1) for classifying the rotors. In some embodiments, rotors can be classified based on three criteria, stability, voltage change, and complex fractionation level. In some embodiments, rotors can also be classified based on rotational patterns of wavefronts and/or any other suitable feature.

At decision branch 410, a rotor can be evaluated for stability based, for example, on determining how many phases out of a total number of phases the rotor appears in. A phase can be, for example, a distinct pattern identified by a far-field electrogram measurement instrument. A rotor that presents in thirty percent (30%) or more of the total phases can be considered to be stable.

In some embodiments, a far-field instrument can be in a stable location (e.g., the coronary sinus) and the electrogram information from the far-field instrument can be monitored. A near-field instrument can be located within a chamber of the patient's heart. A phase can be identified by a unique pattern detected in the far-field electrogram information. When that phase is identified, electrogram information used to build an electro-anatomical model of the patent's heart can be captured from the near-field instrument. The near-field instrument can then be moved to another location within the heart chamber. Once the unique pattern is detected in the far-field electrogram information, the near-field electrogram information can be captured for that location in the patient's heart. The process can be repeated until multiple points of data are collected for areas within the chamber of the patient's heart such that a complete electro-anatomical model (e.g., FIG. 2A) of the patient's heart can be constructed for that unique phase. Additionally, a second unique pattern can be identified in the far-field electrogram information, which can represent a second phase. The process described can be completed to capture information from the near-field instrument to construct an electro-anatomical model (e.g., FIG. 2B) of the patent's heart for the second unique phase. Once multiple electro-anatomical models of the patent's heart are constructed for multiple phases, stable rotors can appear in multiple of the models (e.g., 30% or more of the models).

After evaluating for stability at 410, rotors can be evaluated based on whether they are in a voltage transition zone. A voltage transition zone is a region of heart tissue characterized by a relatively large change in electrical potential (high $\Delta V$) over a relatively short distance. As measured in atrial fibrillation, a change of greater than 0.23 mV can be determined to be a high voltage transition. A voltage transition zone can be associated with healthy tissue meeting dead or scarred tissue. For example, rotor 205 (FIG. 2A) can be migrating along a voltage transition zone, as shown in FIG. 2C, while rotor 215 is not disposed in a voltage transition zone.

Rotors determined to be stable, at 410, are evaluated for voltage transition, at 415. If a rotor is stable and in a voltage transition zone, such as rotor 310, it can be classified as a substrate rotor. Rotors that are determined to be unstable at 410 are evaluated for voltage transition at 420. If a rotor is unstable and not in a voltage transition zone, such as rotor 215, the rotor can be classified as a non-substrate rotor.

If a rotor is stable and not in a voltage transition zone or unstable and in a voltage transition zone, complex fractionation level can be evaluated at 425 and 430 respectively. Either type of rotor evaluated at 425 or 430 with a low complex fractionation can be classified as a substrate rotor. Conversely, either type of rotor evaluated at 425 or 430 with a high complex fractionation can be classified as a non-substrate rotor.

FIGS. 5 A-D describe an example of an embodiment of the present invention. FIG. 5A is an illustration of a human heart having a far-field measurement instrument 520 including multiple electrodes, which can be placed in a stable location, such as, for example, the coronary sinus. FIG. 5B is an illustration of a different view of the human heart having a roving near-field measurement instrument 530 including multiple electrodes, which can be placed at various locations within the heart to gather local electrogram data. FIG. 5D is an illustration of the heart and the various locations 540 within the heart from which electrogram data can be gathered. Local conduction vector data can be calculated and associated with the position of the near-field measurement instrument. FIG. 5C depicts patterns 510 that can be identified on the far-field instrument electrode data 515 simultaneously during near-field signal measurement. FIG. 5D further illustrates that multiple locations and associated near-field data 545 that occurred when the same pattern 510 (FIG. 5C) was occurring on the far-field electrode data can be assembled into a consistent phase map 550, presuming the heart is beating in a certain condition during this phase.

Figure 6B:
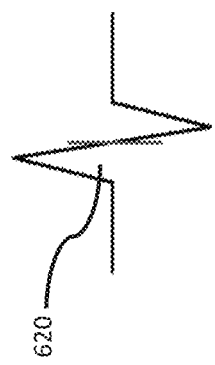
FIG. 6B illustrates the identification of a timing of when heart cells are contracting along a cardiac electrical conduction path, according to an embodiment.
Figure 6C:
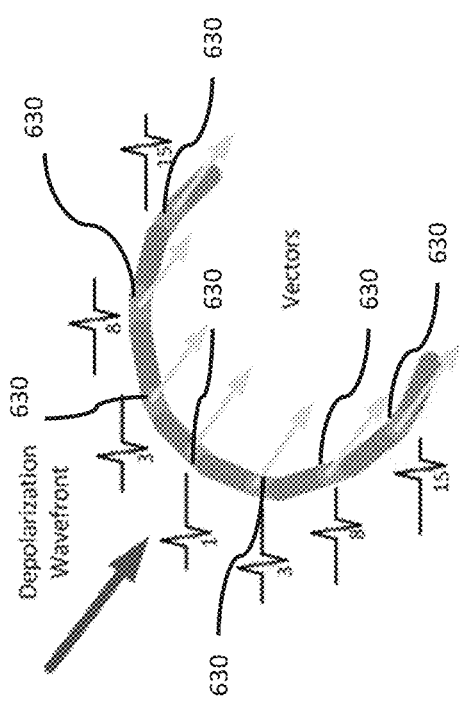
FIG. 6C illustrates multiple signals at different electrodes on a multi-electrode catheter instrument being used to calculate conduction vectors, according to an embodiment.
Figure 6A:
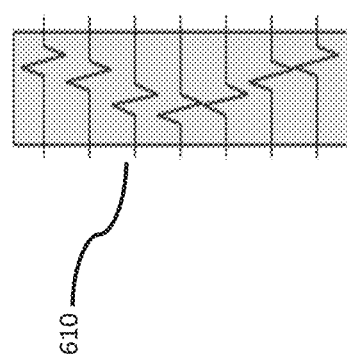
FIG. 6A illustrates a cardiac electrogram signal, according to an embodiment.
Figure 10:
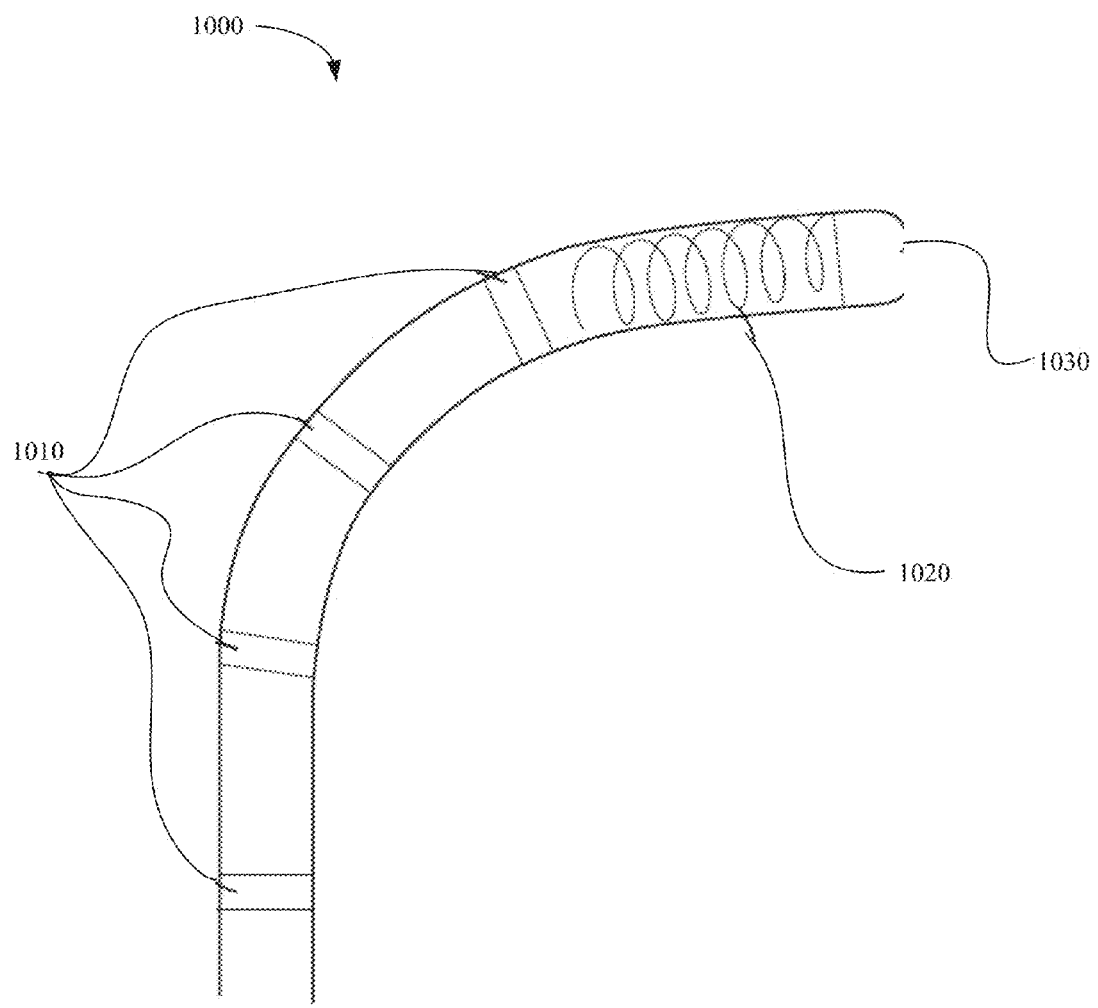
FIG. 10 illustrates an instrument having electrodes, according to an embodiment.

FIGS. 6A-6C depict the intracardiac electrical signals or electrograms 610 acquired by electrodes on cardiac instruments, such as, for example, the instrument depicted in FIG. 10. These signals display the depolarization of the cells in contact with the measurement electrode as the tissue contracts in the heart.

FIG. 6B illustrates how certain morphologies of the electrical signals such as the greatest change in voltage divided by change in time 620 ($\Delta V/\Delta T$) can be used to identify a trigger point for timing and identification of when the heart cells are depolarizing or contracting.

FIG. 6C illustrates how to use known X-Y-Z electrode positions, as measured by a tracking system, and the timing of when the cells in contact with each electrode are depolarizing or triggering to calculate a direction and magnitude of the a cardiac conduction wavefront in the region of the electrodes at each electrode X-Y-Z location. Each calculated direction and magnitude at each electrode is considered a measured conduction vector.

Figure 7:
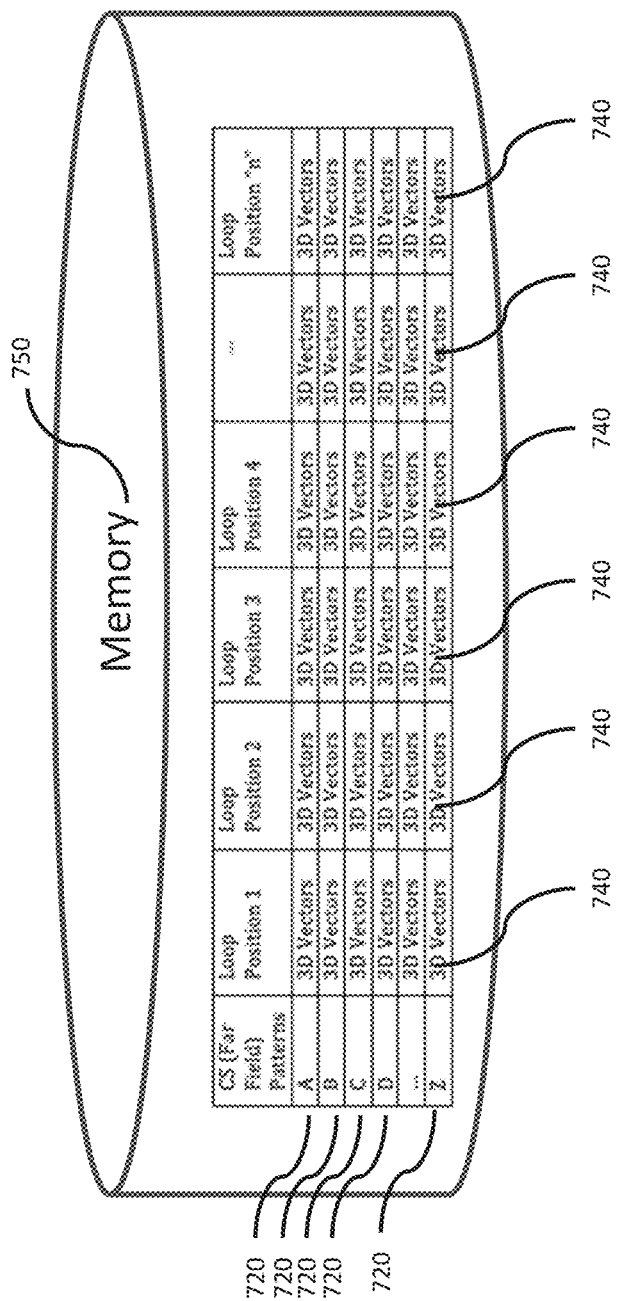
FIG. 7 illustrates a look-up table storing conduction vectors associated with different positions in a heart and times when different patterns are occurring on a stable instrument, according to an embodiment.

FIG. 7 illustrates an example of how conduction vectors 740 can be stored in a look-up table in some embodiments. Memory 750 can be RAM, ROM, a hard drive, a storage drive, and or any other suitable memory device. The position and electrogram data (e.g., data captured at 120 of FIG. 1) can be stored in memory 750. The data can include information from different positions in the heart and associated with different phases 720 or patterns occurring on the far-field instrument's data. The data can be, for example, 3D vector information for each position of the instrument and for each phase. This information can be used, as described in further detail in FIGS. 1 and 11 to construct conduction vector maps and electro-anatomical models.

FIGS. 8A-8C depict how measured conduction vectors of a particular phase can be interpolated over a spatial region in order to create a complete conduction vector map for the entire region. First, conduction vectors can be calculated for each electrode of a roving instrument (e.g., the instrument of FIG. 10) electrode position 840 during a particular phase. Next, the distance from non-measured points to actual electrode positions can be calculated using the formulas shown at 850. Further, the direction value and magnitude value of a conduction vector at a given non-measured point can be calculated using the formulas shown at 860 from all surrounding actual measured conduction vectors. The resulting information can be constructed into a conduction vector map 870.

Multiple conduction vector maps can be constructed over a period of time. The conduction vector maps can be 3D maps, which can further be sequenced by the control unit into a 4D map to show the various states of electrical conductivity of the heart over time.

The 3D and 4D maps created can be superimposed on a model of the patent's heart, such as the model constructed as described in FIG. 1 at 110. The 3D and 4D maps can be displayed in 3D for visualization with bi-color glasses, polarized glasses, shuttered glasses, or any other suitable viewing device that can be used to give true 3D perspective to the viewer.

FIG. 10 is a schematic illustration of the distal portion of an antenna reference instrument 1000, in accordance with an illustrative embodiment of the invention. Antenna reference instrument 1000 can be any medical instrument that can be adapted to be inserted into the thorax of a subject and includes multiple electrodes 1010. In some embodiments, antenna reference instrument can include distal cap electrode 1030. For example, as shown in FIG. 10, antenna reference instrument 1000 can include multiple electrodes 1010, 1030 for sensing current, voltage, or impedance, as well as electromagnetic sensor 1020 for sensing an electromagnetic field. Antenna reference instrument 1000 can include a catheter system, a pacemaker lead system, an implantable cardioverter defibrillator lead system, or any other suitable medical device, depending on the particular embodiment. Antenna reference instrument 1000 can be, for example, the antenna reference instrument disclosed in U.S. patent application Ser. No. 13/747,266 as described above.

Antenna reference instrument 1000 can be the near-field instrument and/or the far-field instrument described herein with respect to the descriptions of other figures.

FIG. 11 describes a method for capturing the electrogram information from the near-field and far-field instruments. This can be used, for example, as the method described in FIG. 1 at 120.

At 1105, a control unit can receive the position coordinates from a near-field instrument. The position coordinates can be in X-Y-Z space and can be identified using the multiple electrodes on the near-field instrument and/or an electromagnetic sensor in the near-field instrument. As described above with respect to FIG. 1, the position coordinates can be obtained with a tracking system designed to locate a medical instrument within the heart of a patient during a cardiovascular procedure.

At 1110, the control unit can receive electrogram information from the far-field instrument. In some embodiments, the electrogram information can continue to stream to the control unit without interruption. In other embodiments, the electrogram information can be sent for shorter periods of time. The control unit can monitor the electrogram information to identify a unique pattern in the electrogram data at 1115. The duration that the unique pattern can be detected in the electrogram information from the far-field instrument can be considered a phase of the monitored heart. In some embodiments, multiple patterns can be identified in the far-field electrogram data, which can be used to identify multiple phases of the monitored heart.

Once a unique pattern is identified at 1115, electrogram information can be received at the control unit from the near-field instrument at 1120. In this way, the electrogram information from the near-field instrument corresponds to the identified pattern or phase of the monitored heart.

At 1125, the control unit can store and associate the unique pattern information, the position coordinates of the near-field instrument, and the electrogram data from the near-field instrument in storage, such as the storage depicted in FIG. 7.

At 1130, the near-field instrument can be moved within the patient's heart chamber, and the control unit can receive the new position coordinates of the near-field instrument. At 1135 the control unit can receive electrogram information from the far-field instrument. In some embodiments, the control unit can receive the electrogram information from the far-field instrument continuously and can continue to receive it between 1110 and 1135. While the near-field instrument remains at the new location within the patient's heart chamber, the control unit can monitor the far-field electrogram information to detect the unique pattern associated with the identified phase from 1115. When the pattern is detected, at 1140, the control unit can receive electrogram information from the near-field instrument at the second location. In this way, the control unit can have information from two different locations within the patient's heart chamber and the information can each be associated with the respective unique pattern identified in the far-field electrogram information.

At 1145, the control unit can store and associate the position coordinates and the electrogram data from the near-field instrument and associate it with the unique pattern information. In some embodiments, the process of obtaining near-field electrogram information associated with different positions within the patient's heart chamber and the unique pattern can be repeated as many or as few times as desired to obtain the information needed to construct a conduction vector map, or any other suitable map or model, of the patient's heart.

At 1150, the control unit can calculate a direction value and a magnitude value of the conduction wavefront at each electrode of the near-field instrument as described in more detail with respect to FIGS. 5 and 8. At 1155, the control unit can generate an interpolated direction value and magnitude value of the conduction wavefront between each of the values calculated at 1150. The interpolation is described in more detail with respect to FIG. 8.

At 1160, the control unit can use the calculated and interpolated values from 1150 and 1155 to generate a conduction vector map as described in more detail with respect to FIG. 8.

While various embodiments have been described above, it should be understood that they have been presented by way of example only, and not limitation. Where methods and/or flowcharts described above indicate certain events and/or flow patterns occurring in a certain order, the ordering of certain events and/or flow patterns may be modified. While the embodiments have been particularly shown and described, it will be understood that various changes in form and details may be made.

For instance, in some embodiments multiple roving instruments may be used. In those embodiments, multiple measurement steps can be done to determine each roving instrument's location. Those measurement steps can be done in parallel, but they need not be done in parallel, depending on the embodiment.

While various embodiments have been described above, it should be understood that they have been presented by way of example only, and not limitation. Furthermore, although various embodiments have been described as having particular features and/or combinations of components, other embodiments are possible having a combination of any features and/or components from any of embodiments where appropriate as well as additional features and/or components.

Where methods described above indicate certain events occurring in certain order, the ordering of certain events may be modified. Additionally, certain of the events may be performed repeatedly, concurrently in a parallel process when possible, as well as performed sequentially as described above. Where methods are described above, it should be understood that the methods can be computer implemented methods having instructions stored on a non-transitory medium (e.g., a memory) and configured to be executed by a processor. For example, some or all of the steps shown and described with reference to FIGS. 1 and/or 4 can be implemented on a computer. For example, a compute device having a processor and a memory can include modules (e.g., hardware and/or software (executing or configured to execute on a processor)) operable to receive data, define models, identify and/or classify rotors, and/or so forth.

Some embodiments described herein relate to computer-readable medium. A computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, PLDs, ROM and RAM devices. Other embodiments described herein relate to a computer program product, which can include, for example, the instructions and/or computer code discussed herein. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

What is claimed is:

1. A system, comprising:
a first instrument having a first plurality of electrodes, the first instrument configured to be placed inside a chamber of a heart;
a second instrument having a second plurality of electrodes, the second instrument configured to be placed in a stable position in relation to the heart;
a control unit configured to:
receive first far-field electrogram information from the second instrument,
identify a unique pattern associated with atrial fibrillation in the first far-field electrogram information,
once the unique pattern in the first far-field electrogram information is identified, receive first near-field electrogram information from the first instrument
store information associated with the unique pattern, first position coordinates of the first instrument associated with the first near-field electrogram information, the far-field electrogram pattern, and the first near-field electrogram information,
receive second far-field electrogram information from the second instrument after the first instrument has moved from the first position coordinates,
identify the unique pattern in the second far-field electrogram information,
once the unique pattern in the second far-field electrogram information is identified, receive second near-field electrogram information from the first instrument,
receive second position coordinates of the first instrument associated with the second near-field electrogram information,
store the second position coordinates of the first and the second near-field electrogram information, and
generate a conduction vector map for a phase of the heart associated with the unique pattern, the conduction vector map generated based on the first near-field electrogram information and the second near-field electrogram information.

2. The system of claim 1, wherein the control unit is further configured to:
calculate a direction value and a magnitude value of a first conduction wavefront at each electrode from the first plurality of electrodes based on the first near-field electrogram information to generate a first set of calculated values,
calculate a direction value and a magnitude value of a second conduction wavefront at each electrode from the first plurality of electrodes based on the second near-field electrogram information to generate a second set of calculated values, and
generate an interpolated direction value and magnitude value between each of the calculated direction values and magnitude values from the first set of calculated values and between each of the calculated direction values and magnitude values from the second set of calculated values to generate a set of interpolated values, the conduction vector map generated using the interpolated values, the first set of calculated values, and the second set of calculated values.

3. The system of claim 1, wherein the control unit is further configured to:
calculate a direction value and magnitude value of a first conduction wavefront at each electrode from the first plurality of electrodes based on the first near-field electrogram information to generate a first set of calculated values,
calculate a direction value and a magnitude value of a second conduction wavefront at each electrode from the first plurality of electrodes based on the second near-field electrogram information to generate a second set of calculated values, and
generate an interpolated direction value and magnitude value between each of the calculated direction values and magnitude values from the first set of calculated values and between each of the calculated direction values and magnitude values from the second set of calculated values to generate a set of interpolated values, the conduction vector map generated using the interpolated values, the first set of calculated values, and the second set of calculated values, the system further comprising:
a display device configured to display the conduction vector map.

4. The system of claim 1, wherein the control unit is further configured to:
calculate a direction value and magnitude value of a first conduction wavefront at each electrode from the first plurality of electrodes based on the first near-field electrogram information to generate a first set of calculated values, calculate a direction value and a magnitude value of a second conduction wavefront at each electrode from the first plurality of electrodes based on the second near-field electrogram information to generate a second set of calculated values, and generate an interpolated direction value and magnitude value between each of the calculated direction values and magnitude values from the first set of calculated values and between each of the calculated direction values and magnitude values of the second set of calculated values to generate a set of interpolated values, the conduction vector map generated using the interpolated values, the first set of calculated values, and the second set of calculated values, the system further comprising:

a display device configured to display the conduction vector map as a three-dimensional image.

5. The system of claim 1, wherein the phase of the heart is a first phase of the heart, the unique pattern is a first unique pattern associated with the first phase of the heart, and the conduction vector map is a first conduction vector map, the control unit is further configured to:

receive third far-field electrogram information from the second instrument while the first instrument is at the first position coordinates, identify a second unique pattern associated with a second phase of the heart in atrial fibrillation in the third far-field electrogram information, the second unique pattern being distinct from the first unique pattern, once the second unique pattern in the third far-field electrogram information is identified and while the first instrument is located at the first position coordinates, receive third near-field electrogram information from the first instrument, store information associated with the second unique pattern, the first position coordinates of the first instrument, and the third near-field electrogram information, receive fourth far-field electrogram information from the second instrument while the first instrument is at the second position coordinates, identify the second unique pattern in the fourth far-field electrogram information, once the second unique pattern in the fourth far-field electrogram information is identified, receive fourth near-field electrogram information from the first instrument while the first instrument is located at the second position coordinates, store information associated with the second unique pattern, the second position coordinates of the first instrument, and the fourth near-field electrogram information, calculate a direction value and magnitude value of a first conduction wavefront at each electrode from the first plurality of electrodes based on the first near-field electrogram information to generate a first set of calculated values, calculate a direction value and magnitude value of a second conduction wavefront at each electrode from the first plurality of electrodes based on the second near-field electrogram information to generate a second set of calculated values, generate an interpolated direction value and magnitude value between each of the calculated direction values and magnitude values from the first set of calculated values and between each of the calculated direction values and magnitude values from the second set of calculated values to generate a first set of interpolated values, the first conduction vector map generated using the first set of interpolated values, the first set of calculated values, and the second set of calculated values, calculate a direction value and magnitude value of a third conduction wavefront at each electrode from the first plurality of electrodes based on the third near-field electrogram information to generate a third set of calculated values, calculate a direction value and magnitude value of a fourth conduction wavefront at each electrode from the first plurality of electrodes based on the fourth near-field electrogram information to generate a fourth set of calculated values, and generate an interpolated direction value and magnitude value between each of the calculated direction values and magnitude values from the third set of calculated values and between each of the calculated direction values and magnitude values from the fourth set of calculated values to generate a second set of interpolated values, generate a second conduction vector map for the second phase of the heart associated with the second unique pattern using the second set of interpolated values, the third set of calculated values, and the fourth set of calculated values, and sequence the first conduction vector map and the second conduction vector map to generate a four-dimensional conduction vector map.

6. The system of claim 1, wherein the control unit is further configured to define an electro-anatomical model of the heart based on the first position coordinates, the second position coordinates, the first near-field electrogram information, and the second near-field electrogram information.

7. The system of claim 1, wherein the control unit is further configured to:

define an electro-anatomical model of the heart based on the first position coordinates, the second position coordinates, the first near-field electrogram information, and the second near-field electrogram information, and identify one or more locations of spiraling conduction vectors in the heart based on surface characteristics of the electro-anatomical model.

8. The system of claim 1, wherein the control unit is further configured to:

define an electro-anatomical model of the heart based on the first position coordinates, the second position coordinates, the first near-field electrogram information, and the second near-field electrogram information, identify one or more locations of spiraling conduction vectors in the heart based on surface characteristics of the electro-anatomical model, and categorize each of the one or more locations of spiraling conduction vectors as one of a substrate rotor or a non-substrate rotor.

9. The system of claim 1, wherein the unique pattern is a swirling conduction pattern.

10. The system of claim 1, wherein the control unit is further configured to:

identify a duration of the unique pattern in the first far-field electrogram information; and define a phase of the heart based on the duration of the unique pattern.

11. A method, comprising:

receiving data associated with first position coordinates of a first instrument within a chamber of a heart;

receiving data associated with electrogram information of a second instrument when the first instrument is at the first position coordinates, the second instrument being located in or on a patient's body such that the second instrument does not move with respect to the heart, to generate first far-field electrogram data;

identifying a unique pattern associated with atrial fibrillation in the far-field electrogram data;

receiving, once the unique pattern in the first far-field electrogram data has been identified, data associated with electrogram info nation of the first instrument to generate first near-field electrogram data;

storing information associated with the unique pattern, the first position coordinates, and the first near-field electrogram data;

receiving data associated with electrogram information of the second instrument when the first instrument is at the second position coordinates, to generate second far-field electrogram data;

identifying the unique pattern in the second far-field electrogram information;

receiving, once the unique pattern in the second far-field electrogram information is identified, data associated with electrogram information of the first instrument to generate second near-field electrogram data; and storing the second position coordinates and the second near-field electrogram data; and generating a conduction vector map for a phase of the heart associated with the unique pattern, the conduction vector map generated based on the first near-field electrogram information and the second near-field electrogram information.

12. The method of claim 11, wherein the first instrument has a plurality of electrodes, the method further comprising:

calculating a direction value and a magnitude value of a first conduction wavefront at each electrode from the plurality of electrodes based on the first near-field electrogram data to generate a first set of calculated values;

calculating a direction value and a magnitude value of a second conduction wavefront at each electrode from the plurality of electrodes based on the second near-field electrogram data to generate a second set of calculated values; and generating an interpolated direction value and magnitude value between each of the calculated direction values and magnitude values from the first set of calculated values and between each of the calculated direction and magnitude values from the second set of calculated values to generate a set of interpolated values, the conduction vector map generated using the interpolated values from the set of interpolated values, the calculated values from the first set of calculated values, and the calculated values from the second set of calculated values.

13. The method of claim 11, wherein the first instrument has a plurality of electrodes, the method further comprising:

calculating a direction value and a magnitude value of a first conduction wavefront at each electrode from the plurality of electrodes based on the first near-field electrogram data to generate a first set of calculated values; calculating a direction value and a magnitude value of a second conduction wavefront at each electrode from the plurality of electrodes based on the second near-field electrogram data to generate a second set of calculated values; and generating an interpolated direction value and magnitude value between each of the calculated direction values and magnitude values from the first set of calculated values and between each of the calculated direction values and magnitude values from the second set of calculated values to generate a set of interpolated values, the conduction vector map generated using the interpolated values from the set of interpolated values, the calculated values from the first set of calculated values, and the calculated values from the second set of calculated values; and displaying the conduction vector map.

14. The method of claim 11, wherein the first instrument has a plurality of electrodes, the method further comprising:

calculating a direction value and a magnitude value of a first conduction wavefront at each electrode from the plurality of electrodes based on the first near-field electrogram data to generate a first set of calculated values;

calculating a direction value and a magnitude value of a second conduction wavefront at each electrode from the plurality of electrodes based on the second near-field electrogram data to generate a second set of calculated values;

generating an interpolated direction value and magnitude value between each of the calculated direction values and magnitude values from the first set of calculated values and between each of the calculated direction values and magnitude values from the second set of calculated values to generate a set of interpolated values the conduction vector map generated using the interpolated values from the set of interpolated values, the calculated values from the first set of calculated values, and the calculated values from the second set of calculated values; and displaying the conduction vector map as a three-dimensional image.

15. The method of claim 11, wherein the phase of the heart is a first phase of the heart, the unique pattern is a first unique pattern associated with the first phase of the heart, and the first instrument has a plurality of electrodes, the method further comprising:

receiving third far-field electrogram information from the second instrument while the first instrument is at the first position coordinates;

identifying a second unique pattern associated with a second phase of the heart in atrial fibrillation in the third far-field electrogram information, the second unique pattern being distinct from the first unique pattern;

receiving, once the second unique pattern in the third far-field electrogram is identified information, data associated with electrogram information of the first instrument at the first position coordinates to generate third near-field electrogram data;

storing information associated with the second unique pattern, the first position coordinates, and the third near-field electrogram data;

receiving fourth far-field electrogram information from the second instrument while the first instrument is at the second position coordinates;

identifying the second unique pattern in the fourth far-field electrogram information;

receiving, once the second unique pattern is identified in the fourth far-field electrogram information, data associated with electrogram information of the first instrument at the second position coordinates to generate fourth near-field electrogram data;

storing the second position coordinates and the fourth near-field electrogram data;

calculating a direction value and magnitude value of a first conduction wavefront at each electrode from the plurality of electrodes based on the first near-field electrogram data to generate a first set of calculated values;

calculating a direction value and a magnitude value of a second conduction wavefront at each electrode from the plurality of electrodes based on the second near-field electrogram data to generate a second set of calculated values;

generating an interpolated direction value and magnitude value between each of the calculated direction values and magnitude values from the first set of calculated values and between each of the calculated direction values and magnitude values from the second set of calculated values to generate a first set of interpolated values, the first conduction vector map generated using the interpolated values from the first set of interpolated values, the calculated values from the first set of calculated values, and the calculated values from the second set of calculated values;

calculating a direction value and magnitude value of a third conduction wavefront at each electrode from the plurality of electrodes based on the third near-field electrogram data to generate a third set of calculated values;

calculating a direction value and a magnitude value of a fourth conduction wavefront at each electrode from the plurality of electrodes based on the fourth near-field electrogram data to generate a fourth set of calculated values;

generating an interpolated direction value and magnitude value between each of the calculated direction values and magnitude values from the third set of calculated values and between each of the calculated direction values and magnitude values from the fourth set of calculated values to generate a second set of interpolated values;

generating a second conduction vector map using the interpolated values from the second set of interpolated values, the calculated values from the third set of calculated values, and the calculated values from the fourth set of calculated values; and sequencing the first conduction vector map and the second conduction vector map to generate a four-dimensional conduction vector map; and outputting data associated with a display of the four-dimensional conduction vector map.

16. The method of claim 11, further comprising:

defining an electro-anatomical model of the heart based on the first position coordinates, the second position coordinates, the first near-field electrogram data, and the second near-field electrogram data; and identifying one or more locations of spiraling conduction vectors in the heart based on surface characteristics of the electro-anatomical model.

17. The method of claim 11, further comprising:

defining an electro-anatomical model of the heart based on the first position coordinates, the second position coordinates, the first near-field electrogram data, and the second near-field electrogram data;

identifying one or more locations of spiraling conduction vectors in the heart based on surface characteristics of the electro-anatomical model; and categorizing each of the one or more locations of spiraling conduction vectors as one of a substrate rotor or a non-substrate rotor.

18. The method of claim 11, wherein the unique pattern is from a plurality of unique patterns and the conduction vector map is from a plurality of conduction vector maps, the method further comprising:

identifying each of the plurality of unique patterns; and generating the plurality of conduction vector maps, each conduction vector map from the plurality of conduction vector maps for a different phase of the heart associated with a different unique pattern from the plurality of unique patterns.

* * * * *